United States Patent
Era et al.

(10) Patent No.: US 10,588,921 B2
(45) Date of Patent: Mar. 17, 2020

(54) DRUG FOR THE TREATMENT OF CHOLESTEROL ACCUMULATION DISORDERS

(71) Applicants: NATIONAL UNIVERSITY CORPORATION KUMAMOTO UNIVERSITY, Kumamoto (JP); NIHON SHOKUHIN KAKO CO., LTD., Tokyo (JP)

(72) Inventors: Takumi Era, Kumamoto (JP); Tetsumi Irie, Kumamoto (JP)

(73) Assignee: NATIONAL UNIVERSITY CORPORATION KUMAMOTO UNIVERSITY, Tokyo (JP)

(*) Notice: Subject to any disclaimer, the term of this patent is extended or adjusted under 35 U.S.C. 154(b) by 415 days.

(21) Appl. No.: 15/101,109

(22) PCT Filed: Dec. 3, 2014

(86) PCT No.: PCT/JP2014/081969
§ 371 (c)(1),
(2) Date: Apr. 17, 2017

(87) PCT Pub. No.: WO2015/083736
PCT Pub. Date: Jun. 11, 2015

(65) Prior Publication Data
US 2017/0216342 A1    Aug. 3, 2017

(30) Foreign Application Priority Data

Dec. 5, 2013  (JP) ................... 2013-252174
Jul. 1, 2014  (JP) ................... 2014-135865

(51) Int. Cl.
| | |
|---|---|
| A61K 31/74 | (2006.01) |
| A61K 9/00 | (2006.01) |
| G01N 33/92 | (2006.01) |
| G01N 33/50 | (2006.01) |
| A61K 31/724 | (2006.01) |
| C12N 5/074 | (2010.01) |

(52) U.S. Cl.
CPC .......... *A61K 31/724* (2013.01); *A61K 9/0019* (2013.01); *C12N 5/0696* (2013.01); *G01N 33/5073* (2013.01); *G01N 33/92* (2013.01); *G01N 2500/04* (2013.01); *G01N 2500/10* (2013.01); *G01N 2800/04* (2013.01)

(58) Field of Classification Search
CPC .... A61K 31/724; A61K 45/06; A61K 9/0019; G01N 33/92; G01N 33/5073; G01N 2800/04; G01N 2500/10; G01N 2500/04; C12N 5/0696
USPC .......................................................... 514/58
See application file for complete search history.

(56) References Cited

U.S. PATENT DOCUMENTS

2012/0077774 A1    3/2012   Maxfield et al.

FOREIGN PATENT DOCUMENTS

| WO | 2012063817 A1 | 5/2012 |
| WO | 2014022841 A1 | 2/2014 |

OTHER PUBLICATIONS

Aqul et al, The Journal of Neuroscience, 2011, 31(25), 9404-9413.*
Szejtli, Medicinal Applications of Cyclodextrins, 1994, 14(3), 353-386.*
Chen et al, PLoS ONE 2010, 5(11), 1-7.*
Irie et al, J. Pharm. Sci., 1992, 81(5), 521-523.*
Peake et al, FEBS Letters, 2010, 584, 2731-2739.*
Aqui et al, The Journal of Neuroscience, 2011, 31(25), 9404-9413.*
Liu, et al., "Reversal of Defective Lysosomal Transport in NPC Disease Ameliorates Liver Dysfunction and Neurodegeneration in the NPC1 Mouse", Proceedings of the National Academy of Science, Feb. 2009, vol. 106, No. 8, pp. 2377-2382.
Fusaki, et al., "Efficient Induction of Transgene-Free Human Pluripotent Stem Cells Using a Vector Based on Sendai Virus, an RNA Virus that Does Not Integrate into Host Genome", Proceedings of the National Academy of Series B, Physical Biology Science, 2009, vol. 85, No. 8, pp. 348-362.
Seki, et al., "Generation of Induced Pluripotent Stem Cells From Human Terminally Differentiated Circulating T Cells", Cell Stem Cell, Physical Biology Science, Jul. 2010, pp. 11-14.
Ban, et al., "Efficient Generation of Transgene-Free Human Induced Pluripotent Stem Cells (iPSCs) by Temperature-Sensitive Sendai Virus Vectors", Proceedings of the National Academy of Science, Aug. 2011, vol. 108, No. 34, pp. 14234-14239.
Irie, et al., "Pharmaceutical Applications of Cyclodextrins.III. Toxicological Issues and Safety Evaluation", Pharmaceutical Sciences, Feb. 1997, vol. 86, No. 2, pp. 147-162.

(Continued)

*Primary Examiner* — Ganapathy Krishnan
(74) *Attorney, Agent, or Firm* — Hunton Andrews Kurth LLP

(57) ABSTRACT

Provided is a pharmaceutical composition for the treatment of disorders such as Niemann-Pick disease and GM1 gangliosidosis which are caused by the storage of cholesterol, such as lysosomal storage disease. Also provided is a method for screening for said pharmaceutical compositions that uses iPS cell strains that phenocopy phentotypes of these disorders. Provided is a pharmaceutical composition for the treatment and/or prevention of lysosomal storage disease, characterized by containing hydroxypropyl-γ-cyclodextrin as an active ingredient. Also provided are an iPS cell strain derived from patients suffering from intractable disorders and prepared using a new temperature-sensitive Sendai virus vector, and a screening method for pharmaceuticals using said iPS cell strain.

12 Claims, 17 Drawing Sheets

Specification includes a Sequence Listing.

(56) References Cited

OTHER PUBLICATIONS

Collins, et al., "Synthesis, Characterization, and Evaluation of Pluronic-Based β-Cyclodextrin Polyrotaxanes for Mobilization of Accumulated Cholesterol from Niemann-Pick Type C Fibroblasts", Biochemistry, Apr. 2013, vol. 52, No. 19, pp. 3242-3253.

* cited by examiner

Fig. 4
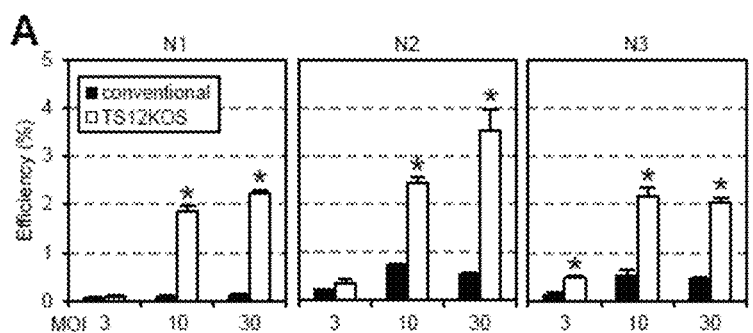
Fig. 5
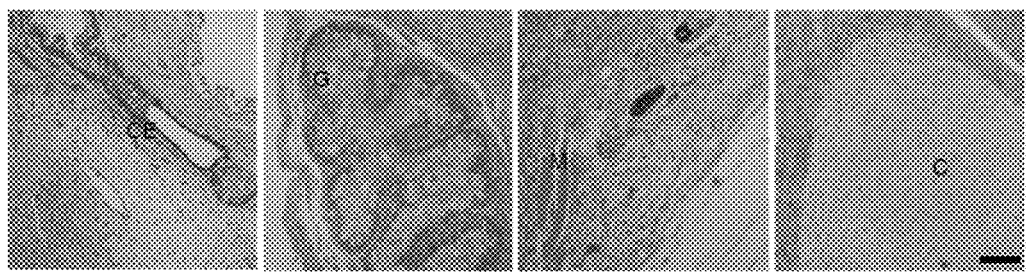
Fig. 6

DRUG FOR THE TREATMENT OF CHOLESTEROL ACCUMULATION DISORDERS

FIELD

The present invention relates to a pharmaceutical composition and a method for treating a disease caused by cholesterol accumulation such as lysosomal diseases and the like. More particularly, the present invention relates to a pharmaceutical composition for treating a disease caused by cholesterol accumulation, comprising hydroxypropyl-γ-cyclodextrin as an active ingredient. The present invention also relates to a method for screening a therapeutic agent for a disease caused by cholesterol accumulation such as lysosomal diseases and the like.

BACKGROUND

When an enzyme associated with a lysosome which is one of intracellular organelles is genetically defective or mutated, substances to be degraded or transported are accumulated as a foreign substance inside or outside cells. A disease of inborn error in metabolism caused by such a phenomenon is known as a lysosomal disease. Examples of the lysosomal disease include Niemann-Pick disease and GM1 gangliosidosis.

Niemann-Pick disease type C (NPC) is one of diseases of congenital lysosomal diseases caused by abnormality of a membrane protein NPC1 molecule which governs transportation of lipids mainly including cholesterol in cells or a secretory protein NPC2 molecule co-existing with NPC1 in endosomes. In patient's cells, free cholesterol and lipids are accumulated in lysosomes. NPC is characterized by hepatomegaly, splenomegaly, and a nervous symptom. NPC is a rare intractable disease which is developed at an infant stage, causes splenohepatomegaly or a progressive nerve disorder, and leads patients to death at around 10 years old. Effective therapy for the present disease has not been established.

A cyclic oligosaccharide, cyclodextrin (CyDs), is a monomolecular host molecule having hydrophobic hollow cavities in the molecule. When a guest molecule is taken into the hollow cavities of CyDs, to form inclusion complexes, a physicochemical nature of the guest molecule varies variously. The supramolecular inclusion phenomenon of CyDs called a molecular capsule is effectively utilized in many fields. Particularly, in drug development, the phenomenon is widely applied to improvement in preparation properties and construction of the drug delivery system.

Recently, Liu et al. have reported that when 2-hydroxypropyl-β-cyclodextrin (HPBCD) is intravenously administered to Npc1 gene-defective (Npc1−/−) mice, this is effective in improving the medical state or prolonging survival, and when HPBCD is directly administered into the brain, the improving effect thereof is increased a few hundreds times, compared with systemic administration (Non-Patent Document 1). Based on the outcome of these fundamental researches, U.S. FDA specially approved humanistic use of HPBCD to NPC child patients (intravenous administration and intrathecal administration). Under such background, also in Japan, in Hospital Affiliated to Medical Department of Sage University, HPBCD injectables were prepared in the hospital, and treatment of NPC child patients was initiated. As a result of continuation for more than 1 year of intravenous instillation of HPBCD (2500 mg/kg per time, 1 to 3 times per week) to NPC child patients, the certain effect of reduction of splenohepatomegaly and improvement in a brain wave in child patients was obtained, but a nervous symptom has not been improved yet. Then, in addition to HPBCD, a glycolipid synthesis inhibitor, Miglustat (50 or 100 mg per time, two times per day), was used concurrently. Furthermore, in order to directly deliver HPBCD into the brain not through the blood brain barrier, intrathecal administration and intraventricular administration via the Ommaya reservoir (30 mg/kg, once per week) are performed, concurrently with intravenous administration of HPBCD. Since treatment with HPBCD is first in Japan and there is no precedent of high dose administration and long term administration, the treatment is continued while the effectiveness and the harmful events of the treatment are closely examined. However, there is also a of the side effect, and HPBCD has not been generalized in Japan yet.

Meanwhile, HPBCD is approved as an additive (solubilizer) of medicaments, but a renal disorder is apprehended. In addition, events such as a pulmonary disorder have also been reported, and in the case of high dose administration or long term administration, safety thereof has become a problem. Accordingly, safer therapeutic agents for NPC in place of HPBCD are desired.

GM1 gangliosidosis is one of Gaucher diseases caused by a mutation of lysosomal-β-glucosidase which is a glycohydrolase, and a mutation of lysosomal-β-galactosidase is the etiology. This is a disease in which by deficiency of beta galactosidase, a glycolipid such as GM1-ganglioside and asialo-GM1-ganglioside, which is a substrate thereof, is accumulated in the brain or internal organs (liver, spleen) and the like, or a mucopolysaccharide such as keratan sulfate or the like is accumulated in the bone. There are three types including the baby type (type 1) which is developed at an early babyhood stage and associated with wide central nervous system disorders including spastic paraplegia, and a cherry red spot of the eyeground, splenohepatomegaly and bone abnormality, the juvenile type (type 2) which is developed from an infant stage and in which a central nervous system disorder progresses, and further, the adult type (type 3) in which a symptom such as dysarthria is manifested from a school age stage and an extrapyramidal symptom is a main symptom.

For these diseases, enzyme replenishment therapy has been main therapy until now, and examples of the problem include a problem that an enzyme preparation hardly reaches a central nerve, and the therapeutic effect on a nervous system including the brain is not seen, and a problem that dripping treatment with an enzyme preparation at the high cost must be continued through life. Accordingly, new therapeutic agents for these lysosomal diseases are desired.

Induced pluripotent stem cells (iPS cells), which are artificially produced from human somatic cells, can be induced to undergo sustained, unlimited growth and exhibit multipotency (i.e., the ability to give rise to various cell types in vitro). Because of these features, iPS cells have potential applications as a source of cell therapy in clinical medicine. The process of iPS cell generation, known as reprogramming, is triggered by the expression of four transcription factors, Oct3/4, Klf4, and c-Myc, which are the same core factors underlying pluripotency in other pluripotent stem cells such as embryonic stem (ES) cells. Overexpression of the four factors was initially mediated by lentivirus and retrovirus vectors in human skin-derived fibroblasts. Although these gene expression systems are stable, they have two potential problems in that the genes encoding the four factors are integrated into the host genome and remain in the resultant iPS cells, and there is a risk of insertional mutagenesis, can facilitate tumorigenesis in vivo The development of efficient and safe reprograming methods based on the Cre/loxP recombination system, adenovirus vector, piggyback transposons, microRNA, and protein has suffered from a low frequency of iPS cell colony generation, a need for repetitive induction, and retention of a short length of foreign DNA in the host genome. A recent study showed that episomal plasmid vectors, which rarely integrate into the host genome, can be used to generate iPS cells from blood cells; however, the efficiency was low (~0.1%) and factors such as p53 knock-down and the transient expression of EBNA were required in addition to the four reprogramming factors.

Sendai virus (SeV) vector technology is analternative strategy developed to overcome the obstacles described above. SeV vectors are minus-strand RNA viruses that express a gene of interest without integration into the host genome and have been used to efficiently generate iPS cells from human skin-derived fibroblasts and blood cells (Non-patent documents 2 and 3). The frequency of iPS cell colony generation with SeV vectors is higher than that achieved with conventional methods using retrovirus and lentivirus vectors (0.1% versus 0.01%). However, the SeV remains inside the cells for more than one month, and thus the establishment of transgene-free iPS cells requires a long time. Recently, the temperature-sensitive SeV (Ts-SeV) system was developed to prevent uncontrolled iPS cell generation due to the sustained cytoplasmic replication of SeV (Non-patent document 4). Ts-SeVs are easily and immediately eliminated from iPS cells derived from cord blood cells and fibroblasts by a temperature upshift, but the efficiency of iPS cell generation with current Ts-SeV vectors is low than that with SeV.

Further, method using the SeV has been reported for producing iPS cells from peripheral blood monocytes. In the method, a SeV vector continuously expressing reprogramming genes Oct4, Sox2, Klf4, and c-Myc is used and the removal of reprogramming gene mounted viral vector from cells is performed by using siRNA (Patent Document 1).

Although skin fibroblasts are the most common cell type used for generating iPS cells, skin biopsies are invasive and are not ideal for children or patients with skin diseases or coagulopathy. Peripheral blood cells is a preferable source cell; however, Ts-SeV vectors have not been reported for generating iPS cells from peripheral blood cells, and prolonged retention of SeV in iPS cells remains a problem when non-temperature sensitive SeV vectors are used.

Numerous iPS cell lines derived from the somatic cells of patients harboring pathogenic mutations, using methods including SeV, were shown to phenocopy the disease. Therefore these cell lines represent a powerful tool not only for cell therapy, but also for biomedical research and drug development. Biomaterial samples obtained from patients with intractable diseases are indispensable for studying the molecular mechanism of diseases and developing new therapeutic agents. However, because the number of samples from such patients is usually limited, disease-derived iPS cells are expected to be useful as a replacement or supplemental source of biomaterials for cell therapy. As just described, iPS cells have been used as a cell source or a cell model of disease. However, its use is limited by inefficient production and the presence of the transgene in cells. Therefore, a method for more efficiently producing iPS cells without introducing genes therein and safe is desired.

CITATION LIST

Patent Literature 1: International Publication WO2012/063817

Non-Patent Literature

Non-Patent Literature 1: Liu et al. Proc Natl Acad Sci USA, 106, 2377 (2009)
Non-Patent Literature 2: Fusaki et al., Proc. Jpn. Acad. Ser. B, Phys. Biol. Sci. 85, 348-362, 2009
Non-Patent Literature 3: Seki et al. Cell Stem Cell 7, 11-14, 2010
Non-Patent Literature 4: Banet al., Proc. Natl. Acad. Sci. USA 108, 14234-14239, 2011
Non-Patent Literature 5: Irie et al., J. Phar. Sci., vol 86, No. 2, pp. 147-162, 1997

SUMMARY OF THE INVENTION

Technical Problem

An object of the present invention is to provide pharmaceutical compositions for treating a disease caused by cholesterol accumulation such as lysosomal diseases and the like, for example, Niemann-Pick disease or GM1 gangliosidosis.

Another object of the present invention is to provide a method for screening those pharmaceutical compositions, more particularly, the object is to provide a method for screening pharmaceutical compositions for treating the disease caused by cholesterol accumulation such as lysosomal diseases and the like, using an iPS cell strain mirroring the phenotype of the disease.

The present invention also relates to a method for effectively preparing an iPS cell strain used in the above-described screening method, more particularly, it relates to a method for effectively preparing an iPS cell strain used in the above-described screening method, using a temperature-sensitive Sendai virus having only specified reprogramming factors.

Another object of the present invention is to provide a transgene-free iPS cell strain, which is an effective cell model of intractable diseases.

Solution to Problem

The present inventors have developed a new Sendai virus vector, TS12KOS, which improves the efficiency of preparing iPS cells, and can be easily removed from cells without being integrated into intracellular DNAs. The present inventors have also prepared an iPS cell strain exhibiting the phenotype of intractable diseases, from patients with the diseases, using the TS12KOS vector, and developed a method for screening therapeutic agent candidates for the diseases using the cell strain. The present inventors have, further, used such a method to find out a pharmaceutical composition for treating a disease caused by cholesterol accumulation such as lysosomal diseases and the like, for example, Niemann-Pick disease and GM1 gangliosidosis.

The present invention includes the following:
(1) A pharmaceutical composition for treating or preventing a lysosomal disease, comprising hydroxypropyl-γ-cyclodextrin as an active ingredient.
(2) The pharmaceutical composition according to (1), wherein the lysosomal disease is Niemann-Pick disease.

(3) The pharmaceutical composition according to (1), wherein the lysosomal disease is GM1 gangliosidosis.

(4) The pharmaceutical composition according to any one of (1) to (3), wherein the pharmaceutical composition is an injectable and is administered for a long term.

(5) A method for screening a drug candidate for an intractable disease, comprising differentiating iPS cells into an arbitrary lineage, said iPS cells prepared by a step of preparing iPS cells comprising the following steps:

(i) a step of infecting cells derived from an intractable disease patient with a temperature-sensitive Sendai virus vector to reprogram the cells, wherein the vector comprises each gene of an NP gene, a P gene comprising three mutations generating alanine residues (D433A, R434A, and K437A), an M gene, an HN gene and an L gene, and carries sequences encoding three reprogramming genes, KLF4, OCT3/4 and SOX2 in this order direction between the P gene and the M gene, and (ii) a step of culturing the cells infected with the vector at a temperature exceeding 37° C., thereby removing the vector carrying the reprogramming genes from the cells to prepare transgene-free iPS cells, then, culturing the cells together with a target substance, and then, detecting an influence of the target substance on the cells.

(6) The screening method according to (5), wherein culturing at the step (ii) is at 38° C.±0.5° C.

(7) The screening method according to (5) or (6), wherein the cells derived from an intractable disease patient are skin fibroblasts.

(8) The screening method according to (5) or (6), wherein the cells derived from an intractable disease patient are cells derived from peripheral blood.

(9) The screening method according to any one of (5) to (8), wherein the intractable disease is a lysosomal disease.

(10) The screening method according to (9), wherein the lysosomal disease is Niemann-Pick disease or GM1 gangliosidosis.

(11) iPS cells derived from a lysosomal disease patient prepared by steps comprising:

(i) a step of infecting cells derived from a lysosomal disease patient with a temperature-sensitive Sendai virus vector to reprogram the cells, wherein the vector comprises each gene of an NP gene, a P gene comprising three mutations generating alanine residues (D433A, R434A and K437A), an M gene, an HN gene and an L gene, and carries sequences encoding three reprogramming genes, KLF4, OCT3/4 and SOX2 in this order direction between the P gene and the M gene, and (ii) a step of culturing the cells infected with the vector at a temperature exceeding 37° C., thereby removing the vector carrying the reprogramming genes from the cells to prepare transgene-free iPS cells.

(12) The iPS cells according to (11), wherein the cells derived from a lysosomal disease patient are skin fibroblasts.

(13) The iPS cells according to (11), wherein the cells derived from a lysosomal disease patient are cells derived from peripheral blood.

(14) The iPS cells according to any one of (11) to (13), wherein the lysosomal disease is Niemann-Pick disease or GM1 gangliosidosis.

(15) The iPS cells according to (14), wherein the lysosomal disease is Niemann-Pick disease, and an NPC1 gene and an NPC2 gene have a mutation.

(16) The iPS cells according to (15), wherein the lysosomal disease is Niemann-Pick disease, and when differentiated into hepatocyte-like cells, the iPS cells exhibit the following phenotypes:

(a) intracellular cholesterol accumulation is increased,
(b) the autophagy function of the cells is impaired, and
(c) ATP production in the cells is reduced.

Advantageous Effect of Invention

The composition containing hydroxypropyl-γ-cyclodextrin as an active ingredient of the present invention is effective for iPS cells mirroring the phenotype of the lysosomal disease, particularly Niemann-Pick disease or GM-1 gangliosidosis, and is also effective as a therapeutic agent for those diseases.

In addition, by the method of the present invention using the temperature-sensitive Sendai virus vector, iPS cells can be effectively prepared from cells from an intractable disease patient, and the prepared iPS cells mirror the phenotype of the disease, and at the same time, are transgene-free. When these iPS cells are used, drug candidates for the disease can be easily screened. Furthermore, the prepared iPS cells themselves do not undergo canceration, and are safe.

BRIEF DESCRIPTION OF DRAWINGS

FIG. 4 It shows nested RT-PCR analysis of the elimination of SeV vectors after the temperature shift from 37° C. to 38° C. in human fibroblast-derived iPS cells. It shows number of clones in which vectors are eliminated after passages (one or two) passages.

FIG. 5 It shows iPS cell generation from human peripheral blood cells. Experiments were conducted in triplicate (mean±SD). (A) N1, N2, and N3 indicate individual healthy volunteers. *P<0.01, TS12KOS vector versus conventional vector, Student's t-test. (B) Nested RT-PCR analysis of the elimination of SeV vector after the temperature shift from 37° C. to 38° C. It shows number of clones in which vectors are eliminated after passages (one or two) passages.

FIG. 6 It shows tissue morphology of a representative teratoma derived from an iPS cell ("iPSC") line generated with TS12KOS vector after hematoxylin and eosin-staining. The descendants of all three germ layers were observed in the teratoma. The iPSC line is derived from human fibroblasts, BJ. CE, cuboidal epithelium (ectoderm); G, glandular structure (endoderm); M, muscle tissue (mesoderm); C, cartilage (mesoderm). Scale bars, 100 μm.

DESCRIPTION OF EMBODIMENTS

Figure 1:
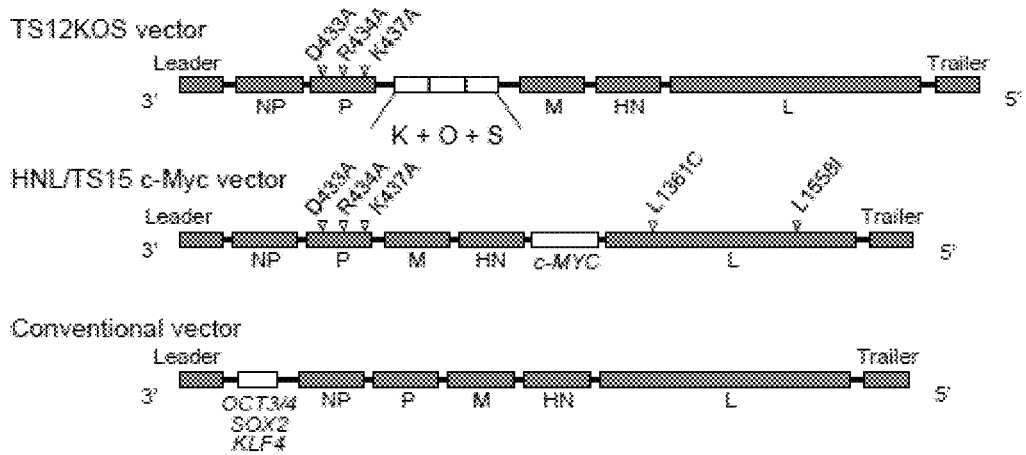
FIG. 1 It shows comparison of schematic structures of the temperature sensitive Sendai virus (TS-SeV) vector and TS12KOS of the present invention with a conventional vector. The TS12KOS vector contains three point mutations in the RNA polymerase-related gene (P) and carries the coding sequences of KLF4(K), OCT3/4(O), and SOX2(S) in the KOS direction. In comparison, the HNL/TS15 c-Myc vector carries two additional mutations, L1361C and L1558I, in the large polymerase (L) gene and an exogenous c-MYC cDNA sequence inserted between the hemagglutinin-neuraminidase (HN) and L genes. The conventional vector individually carries three reprogramming factors.

The present invention will be illustrated in detail below, but the present invention is not limited to aspects described below.

The vector carrying reprogramming genes used for preparing iPS cells in the present invention is a temperature-sensitive Sendai virus (TS-SeV) vector which has an NP gene, a P gene and an L gene derived from a Sendai virus (SeV), and is defective in an F gene. The vector comprises three mutations generating alanine residues (D433A, R434A and K437A) in the L gene. The Sendai virus vector (SeV) having these three mutations has a characteristic that it exhibits moderate expression of GFP at 37° C., and exhibits weak expression at a temperature exceeding 38° C. The vector used in the present invention is characterized in that it further carries sequences encoding three reprogramming genes, KLF4 (K), OCT3/4 (O) and SOX2 (S) in a KOS direction, between the P gene and the M gene. Thereby, even cells derived from an intractable disease patient can be effectively reprogrammed, and at the same time, the virus vector can be easily removed from the cells.

The Sendai virus vector is a gene introduction and expression vector which can express an arbitrary gene by inserting the gene into a genome of the Sendai virus, or substituting a gene of the Sendai virus with the gene. The Sendai virus has respective genes of NP, P, M, HN, F and L, and the NP, P and L genes of the same virus are genes involved in transcription and replication of the Sendai virus, while the M, F and NH genes are genes involved in formation of virions. Accordingly, the Sendai virus vector defective in the F gene cannot form novel virions by itself alone after infection of cells therewith, and becomes non-propagating.

In addition, for the TS-Sev vector used in the present invention, the Sendai virus to which other mutation or alteration is added can also be used, as far as it has three mutations in the L gene contributing to temperature sensitivity, and three reprogramming genes, KLF4 (K), OCT3/4 (O) and SOX2 (S) carried between the P gene and the M gene in a KOS direction, and has a nature that the virion forming ability is deleted.

The reprogramming gene to be inserted into SeV used in the present invention is characterized in that it comprises each gene of Oct3/4, Sox2 and Klf4 of a human, a mouse or an arbitrary mammal in a specified sequence order. In addition, it may comprise a reprogramming gene involved in tumor formation, other than it, for example, a c-Myc gene or an L-Myc gene, preferably comprises only Oct3/4, Sox2 and Klf4 as the reprogramming gene, and do not comprise a gene having the tumor forming activity other than it.

The TS-SeV vector having the above characteristics can be prepared using the known method.

In reprogramming of cells, differentiated cells to be a subject of reprogramming are infected with the TS-SeV vector carrying reprogramming genes in a form of the virion. The cells to be a subject of reprogramming are cells derived from a patient with an intractable disease, preferably, skin fibroblasts or cells derived from peripheral blood. The cells derived from peripheral blood may be any of T lymphocyte cells and monocyte cells. Peripheral blood is lower in invasiveness, compared with the skin fibroblasts, and is also suitable for infant patients and patients having a skin disease or a coagulation disorder. Using the TS-SeV vector in the present invention, iPS cells can be prepared at the high efficiency of "~4%" in the skin fibroblasts, and "~2%" in the peripheral blood cells.

An operation such as infection of cells with the TS-SeV vector in the present invention, and culturing, treatment, selection etc. of the infected reprogrammed cells can be performed according to the conventional method.

In addition, when cells are reprogrammed using the TS-SeV vector in the present invention, an introduced gene or a part thereof is not inserted into unspecified sites of chromosomes. Further, one aspect of the TS-SeV vector in the present invention does not use a c-Myc gene or an L-Myc gene having the tumor forming activity. For this reason, the resulting iPS cells have no possibility that they cause canceration, and are extremely safe.

Removal of the vector carrying the reprogramming genes can be performed by shifting (elevating) a temperature for culturing cells. For example, the vector can be completely removed, for example, by elevating a temperature of cells which are being cultured and passaged at 37° C. to a temperature exceeding 37° C., preferably a temperature exceeding 37° C. and not higher than 39° C., more preferably 38° C.±0.5° C., and further preferably 38° C. A culturing term at a temperature exceeding 37° C. is not particularly limited as far as the vector can be removed, and when the term is expressed by the number of days, it is for example 2 to 20 days, preferably 2 to 15 days, and further preferably 3 to 5 days, and on the other hand, when the term is expressed by the passaging number, it is preferably 1 to 3 passages, and further preferably 1 to 2 passages. By separating single clones after the reprogrammed cells are treated at a temperature exceeding 37° C., clones from which the vector has been completely removed can be obtained. Confirmation of vector removal can be performed by the conventional method, for example, by detecting an arbitrary gene in the vector by RT-PCR. Like this, when the TS-SeV vector in the present invention is used, transgene-free iPS cells can be prepared in a short term of within one week from isolation of iPS cell colonies. In addition, unlike the previous technique not using the SeV vector, this system does not require a plurality of infection cycles, and further, the efficiency of preparing iPS cells is 20 to 100 times of the case where iPS cells are obtained using the technique such as a retrovirus, a lentivirus, or a plasmid vector.

iPS cells prepared from cells of an intractable disease patient, using TS-SeV in the present invention, can exhibit the characteristic of the disease (phenotype). The phenotype can be confirmed by differentiation-inducing the prepared iPS cells into desired cell lineages. Differentiation inducement of iPS cells can be performed according to the conventional method. For example, differentiation inducement into a liver lineage can be performed by culturing the prepared iPS cells in a hepatocyte differentiation-inducing medium. Thus differentiation-induced cells exhibit the characteristic of a disease (phenotype) from which the cells are derived. For example, hepatocyte-like cells which were induced from iPS cells derived from a Niemann-Pick disease type C patient accumulate cholesterol, and as a result, exhibit a functional disorder. Examples of the functional disorder include a functional disorder of autophagy and ATP production. As other example, liver-like cells which were induced from iPS cells derived from a GM-1 gangliosidosis patient exhibit the characteristic of abnormality of autophagy (phenotype).

Since cells which were differentiation-induced from iPS cells derived from an intractable disease patient become a cell model of the disease, they become a powerful tool for research and screening of drug candidates.

For example, as will be described in the following Examples in detail, both 2-hydroxy-γ-cyclodextrin (HPGCD) and 2-hydroxypropyl-β-cyclodextrin (HPBCD) removed cholesterol accumulated in hepatocyte-like cells derived from NPC, and recovered the function of the hepatocyte-like cells. This shows that HPGCD is a promising new candidate for treatment of NPC.

The pharmaceutical composition of the present invention contains hydroxypropyl-γ-cyclodextrin as an active ingredient, and can be used as a therapeutic agent for a lysosomal disease. Examples of the lysosomal disease include Niemann-Pick disease, Tay-sachs disease, sialidosis or GM-1 gangliosidosis.

As shown below, HPGCD exhibited the activity equal to or more than that of HPBCD, on hepatocyte-like cells which had been differentiation-induced from NPC patient-derived iPS cells, which exhibit the phenotype of Niemann-Pick disease. Meanwhile, 2-hydroxy-α-cyclodextrin (HPACD) exhibited no activity at all. This result is surprising in view of the result that the effect of HPGCD is a several tenth part or less, compared with that of HPBCD, in a report (Non-Patent Document 5) confirming the cholesterol dissolution activities of HPBCD and HPGCD using cultured cells.

One of the most important requirements for drug candidates is no or acceptable low levels of intrinsic cytotoxicity. Interaction between cyclodextrin and a cell membrane is an initial stage of such cell damage. The in vitro dissolution activity of isolated erythrocyte is an index of toxicity of each cyclodextrin, and the hemolytic activity of hydroxypropyl-cyclodextrin is in the order of HPBCD>HPACD>HPGCD (Non-Patent Document 5). The previous research showed that γ-cyclodextrin is safer than α- or β-cyclodextrin in acute intravenous administration to rats, and it has been reported that an intravenous dose showing lethality to 50% of population (LD50 value) is 1000, 788, and >3750 mg/kg, respectively, for α-, β-, and γ-cyclodextrins. Accordingly, HPGCD is more excellent as a therapeutic agent for Niemann-Pick disease, as compared with HPBCD.

The composition of the present invention preferably takes a form of a preparation for injection, but is not limited to this. The preparation for injection of the present invention can be intravenously, intramuscularly or subcutaneously administered. In addition, the pharmaceutical composition of the present invention can take a form of any of a water-soluble preparation or a lyophilized preparation, and preferably, examples thereof include aqueous injectables, and lyophilized injectables soluble at use.

The composition of the present invention may comprise saccharides, antiseptics, stabilizers, and antistatic agents which are usually used in injectables. The composition of the present invention can also contain pharmacologically acceptable pH adjusting agents. The pH adjusting agents used in the present invention are not particularly limited as far as they are substances which can be used in utility of medicines, and are pharmacologically acceptable, and are preferably sodium hydroxide, a carbonate buffer, a phosphate buffer, a citrate buffer, an acetate buffer and hydrochloric acid. These pH adjusting agents may be used alone, or may be used by mixing two or more kinds. The composition of the present invention can also contain osmotic pressure adjusting agents or isotonizing agents, and can contain, for example, at least one kind of sodium chloride, dextrose and the like.

The effective dose of the pharmaceutical composition of the present invention can be appropriately selected depending on a kind of a disease, an degree of a sickness, a treatment plan, a weight, an age, a sex, and the (hereditary) racial background of a patient, and a pharmaceutical effective dose is generally determined based on factors such as a clinically observed symptom, a degree of progression of a disease etc. A dose per day is, for example, 0.1 g/kg to 10 g/kg (3 g to 600 g in an adult having a weight of 60 kg), preferably 0.2 g/kg to 10 g/kg, more preferably 0.2 g/kg to 5 g/kg, and further preferably 0.2 g/kg to 2 g/kg. A dose may be administered once, or may be administered by dividing into plural times, or may be continuously administered by dripping etc. over time, and preferably may be administered by dripping over a period of a few hours or longer, for example, over a period of a few hours to about 10 hours. In addition, administration may be daily or intermittent administration, and can be appropriately selected depending on the state of an administration subject, and is preferably intermittent administration. For example, it is also possible to administer 0.5 g/kg to 10 g/kg per one time, 1 to 3 times per week.

In addition, since the pharmaceutical composition of the present invention is excellent in safety, it can be administered for a long term. That is, the lysosomal disease targeted by the pharmaceutical composition of the present invention is a hereditary disease, and administration is required in many cases as far as patients are alive. Since the pharmaceutical composition of the present invention is excellent in safety, it is particularly excellent in such use. A term during which the medicament of the present invention can be administered is not particularly limited, but the medicament of the present invention can be administered over a long term, such as at least over a few weeks or longer, preferably a few months or longer, and more preferably a plurality of years or longer.

EXAMPLES

Hereinafter, the present invention will be described in further detail with reference to the Examples. However, the present invention is not limited thereto.

1. Material and Method (1) Generation of Sendai Virus (SeV) Vectors

Generation and production of temperature-sensitive Sendai virus vectors were performed as described in the report by Ban et al (non-patent literature 4). The conventional type of SeV vectors carrying Oct3/4, Sox2, Klf4 and c-Myc were also generated as described in the report by Fusaki et al. (non-patent literature 2). To generate TS12 vector, three mutations including D433A, R434A and K437A were introduced into the polymerase-related gene P. For TS15 vector generation, other mutations, L1361C, and L1558I, were inserted into polymerase-related genes L of TS12. For "three-in-one" vector, human KLF4, OCT3/4 and SOX2 genes were inserted between P and M gene-encoding region in order as described in FIG. 1A. Each gene was sandwiched by E (End), I (Intervening) and S (Start) sequences.

(2) Maintenance of Human iPS Cells

Human iPS cells were maintained on MMC-treated MEF feeder cells in human iPS medium containing DMEM/F12 (SIGMA) supplemented with 20% KNOCKOUT™ serum replacement (KSR, Invitrogen), 2 mM L-glutamine (Life technologies), 0.1 mM nonessential amino acids (NEAA, SIGMA), 0.1 mM 2-mercaptoethanol (SIGMA), 0.5% penicillin and streptomycin (Nacalai Tesque, Japan) and 5 ng/ml basic fibroblast growth factor (bFGF, WAKO, Japan).

(3) Differentiation into Hepatocyte-Like Cells

For hepatocyte-like cell (HLC) induction, the culture medium of semi-confluent human iPS cells were switched from the iPS medium to the definitive endoderm differentiation medium containing RPMI1640 supplemented with 2% B27 (Life technologies), 100 ng/ml Activin A and 1 mM Sodium butyrate (NaB, SIGMA). The NaB concentration is changed in 0.5 mM on day 2. On day 4, the cells were harvested and re-seeded onto Matrigel-coated dishes in hepatic differentiation medium containing DMEM supplemented with 20% KSR, 1 mM glutamine, 1 mM NEAA, 0.1 mM 2-mercaptoethanol (SIGMA), 1% Dimethyl sulfoxide (DMSO, SIGMA). CXCR4 expressions were examined by FACS on day 4. On day 11, the cells were harvested and re-cultured in the hepatic maturation medium containing L15 medium (SIGMA) supplemented with 8.3% FBS, 8.3% tryptose phosphate broth (SIGMA), 10 mM hydrocortisone 21-hemisuccinate (SIGMA), 1 mM insulin (SIGMA), 2 mM glutamine, 10ng/ml Hepatocyte growth factor (HGF, R & D) and 20 ng/ml Oncostatin M (OSM, R & D). On day 18, the cells were used for various experiments. For the hydroxypropyl cyclodextrin treatments, HLCs were cultured with 0.1 mM or 1 mM of the hydroxypropyl cyclodextrins for four days. For Annexin and TUNEL stainings, HLCs are cultured for four days and a week from day 18, respectively.

(4) Karyotype Analysis

G band analyses of chromosome were performed by Nihon Gene Research Laboratories. Inc. (Sendai, Japan), according to the manufacturer's protocol.

(5) Teratoma Formation

Healthy volunteer and patient-derived iPSC lines grown on MEF feeder layers were collected by collagenase IV treatment and injected into the testis of NOD-SCID immunodeficient mice. Palpable tumors were observed about 8-12 weeks after injection. Tumor samples were collected, fixed in 10% formalin, and processed for paraffin-embedding and hematoxylin-eosin staining following standard procedures.

(6) RNA Isolation and PCR

Total RNA was purified with Sepasol® Super G reagent (Nacalai Tesque, Japan). Total RNA was transcribed to DNA with Superscript III (Invitrogen) and randam primers (Invitrogen). RT-PCR was performed with QuickTaq™ (TOYOBO, Japan) as described in the report of Hamasaki et al. (Stem Cells, 30, 2437-2449, 2012). Primers used for Oct3/4, Sox2, Klf4 and c-Myc were designed to detect the expressions of endogenous genes, but not of transgenes. To detect SeV genome, nested RT-PCR was performed. The sequences of primers and amplification conditions are listed in Table 1 (The sequences are numbered as Sequence Nos. 1 to 48 in order from the top).

TABLE 1

The sequences of primer sets for RT-PCR, nested PCR, and qPCR

| Genes | Sequences (Forward; F, Reverse; R) | Annealing (° C.) | Cycle | Product size (bp) |
|---|---|---|---|---|
| SeV | F: GGATCACTAGGTGATATCGAGC<br>R: ACCAGACAAGAGTTTAAGAGATATGTATC | 58 | 30 | 181 |
| Nested | F: TCGAGCCATATGACAGCTCG<br>R: GAGATATGTATCCTTTTAAATTTTCTTGTCTTCTTG | 58 | 30 | 148 |
| OCT3/4 | F: GACAGGGGGAGGGGAGGAGCTAGG<br>R: CTTCCCTCCAACCAGTTGCCCCAAAC | 55 | 33 | 144 |
| SOX2 | F: GGGAAATGGGAGGGGTGCAAAAGAGG<br>R: TTGCGTGAGTGTGGATGGGATTGGTG | 55 | 33 | 151 |
| KLF4 | F: GATTACGCGGGCTGCGGCAAAACCTACACA<br>R: TGATTGTAGTGCTTTCTGGCTGGGCTCC | 56 | 35 | 357 |
| c-MYC | F: GCGTCCTGGGAAGGGAGATCCGGAGC<br>R: TTGAGGGGCATCGTCGCGGGAGGCTG | 56 | 33 | 328 |
| NANOG | F: CAGCCCCGATTCTTCCACCAGTCCC<br>R: CGGAAGATTCCCAGTCGGGTTCACC | 60 | 30 | 391 |
| GDF3 | F: CTTATGCTACGTAAAGGAGCTGGG<br>R: GTGCCAACCCAGGTCCCGGAAGTT | 56 | 35 | 631 |
| REX1 | F: CAGATCCTAAACAGCTCGCAGAAT<br>R: GCGTACGCAAATTAAAGTCCAGA | 55 | 30 | 306 |
| SALL4 | F: AAACCCCAGCACATCAACTC<br>R: GTCATTCCCTGGGTGGTTC | 58 | 30 | 138 |
| DNMT3b | F: TGCTGCTCACAGGGCCCGATACTTC<br>R: TCCTTTCGAGCTCAGTGCACCACAAAC | 55 | 33 | 242 |
| SOX17 | F: CGCTTTCATGGTGTGGGCTAAGGACG<br>R: TAGTTGGGGTGGTCCTGCATGTGCTG | 50 | 40 | 186 |
| CXCR4 | F: CACCGCATCTGGAGAACCA<br>R: CTGACAGGTGCAGCCTGTA | 55 | 30 | 272 |
| HNF4a | F: CTGCTCGGAGCCACCAAGAGATCCATG<br>R: ATCATCTGCCACGTGATGCTCTGCA | 62 | 30 | 370 |

TABLE 1-continued

The sequences of primer sets for RT-PCR, nested PCR, and qPCR

| Genes | Sequences (Forward; F, Reverse; R) | Annealing (° C.) | Cycle | Product size (bp) |
|---|---|---|---|---|
| HNF6 | F: CGCTCCGCTTAGCAGCAT<br>R: CCCTGCTGAAGTGTGTGTCT | 55 | 40 | 504 |
| AFP | F: AGAACCTGTCACAAGCTGTG<br>R: GACAGCAAGCTGAGGATGTC | 55 | 25 | 675 |
| ALB | F: CCTTTGGCACAATGAAGTGGGTAACC<br>R: CAGCAGTCAGCCATTTCACCATAGG | 62 | 35 | 354 |
| β-ACTIN | F: CAACCGCGAGAAGATGAC<br>R: AGGAAGGCTGGAAGAGTG | 60 | 25 | 455 |
| PAX6 | F: GTCCATCTTTGCTTGGGAAA<br>R: TAGCCAGGTTGCGAAGAACT | 50 | 40 | 110 |
| ZIC1 | F: CTGGCTGTGGCAAGGTCTTC<br>R: CAGCCCTCAAACTCGCACT | 57 | 40 | 97 |
| ZNF 521 | F: ACCTCCGTGTCCAGTACGAC<br>R: ATGTCAGGGGTTTGTTGAGC | 50 | 40 | 125 |
| OTX2 | F: GCCAATCCTTGGTTGAATCTTAGG<br>R: CAATCAGTCACACAATTCACACAGC | 45 | 40 | 120 |
| NEUROGENIN1 | F: AGCCTGCCCAAAGACTTGCTCC<br>R: CCTAACAAGCGGCTCAGGTATCCC | 44 | 40 | 201 |
| HES5 | F: CTCAGCCCCAAAGAGAAAAA<br>R: GACAGCCATCTCCAGGATGT | 45 | 40 | 168 |

(7) Genomic Sequencing

The mutations of NPC1 gene in NPC-derived iPSC lines were confirmed by direct sequencing. The genomic DNAs extracted were amplified by PCR and the resultant PCR products sequenced by ABI PRISM™ 310 Genetic Analyzer (Applied Biosystems). Sequencing primers and amplification conditions are listed in Table 2 (The sequences are numbered as Sequence Nos. 49 to 56 in order from the top.).

TABLE 2

The sequences of primer sets for genomic sequencing

| Genes | Sequences (Forward; F, Reverse; R) | Annealing (° C.) | Cycle | Product size (bp) |
|---|---|---|---|---|
| exon5 sequence | F: TGCCTCGTG AATTACAGCAA<br>R: CAAGCACTG GTGAGCCACT | 52 | 30 | 315 |
| exon13 sequence | F: GCCCGAGCA GACCTAGAAAT<br>R: ATGCTGAGC CCTGTGAGAAT | 56 | 35 | 382 |
| exon22 sequence | F: GGTGAGTCT TGTAGACAGCC<br>R: ATGGCGATG GTGGCACACAT | 58 | 30 | 297 |
| exon23 sequence | F: CAGGCTTTT GGCTGTGTGTA<br>R: GGATTACTT TGTGGTGCGACT | 55 | 30 | 375 |

(8) Cell Staining and Immunocytochemistry

Alkaline phosphatase staining was performed using the Leukocyte Alkaline Phosphatase kit (SIGMA). For immunocytochemistry, cells were fixed with PBS containing 4% paraformaldehyde for 30 min at 4° C. For the molecules localized in nucleus, samples were treated with 0.2% Triton X-100 for 15 min at room temperature (RT). The cells were washed three times with PBS containing 2% FBS and then incubated overnight at 4° C. in PBS containing 2% FBS with primary antibodies. Nucleuses were stained with Propidium Iodide (PI, WAKO, Japan) and 1 mg/ml Hoechst 33258 (Invitrogen). The list of the primary and secondary antibodies is described in Table 3. For Filipin staining, samples were washed with PBS three times after the fixing and incubated with PBS containing 1.5 mg/ml glycine for 10 min at RT. The samples were then treated with PBS containing 10% FBS and 50 mg/ml Filipin (SIGMA). The data was calculated by UV absorption (360/460) and analyzed with Developer Toolbox software of IN CELL ANALYZER 6000 (GE Healthcare). The number of insoluble p62 granules were counted by IN CELL ANALYZER 6000 (GE Healthcare). To investigate glycogen accumulation, Periodic acid Schiff (PAS) staining of hepatocyte-like cells were performed by PAS staining solution (Muto Pure chemicals, Tokyo, Japan), according to the manufacturer's protocol.

TABLE 3

List for antibodies applied.

| Antibody | Species | Dilution | Vendor |
|---|---|---|---|
| Anti-SSEA4 | Mouse | 1:500 | MILLIPORE |
| Anti-TRA-1-60 | Mouse | 1:500 | MILLIPORE |
| Anti-Nanog | Goat | 1:1000 | R&D systems |
| Anti-Oct3/4 | Mouse | 1:500 | Santa Cruz |
| Anti-CXCR4 | Mouse | 1:300 | R&D systems |
| Anti-Albumin | Mouse | 1:500 | SIGMA |
| Anti-Alpha fetoprotein | Mouse | 1:500 | SIGMA |

TABLE 3-continued

List for antibodies applied.

| Antibody | Species | Dilution | Vendor |
| --- | --- | --- | --- |
| Anti-LC3 | Rabbit | 1:500 | Cell Signaling Technology |
| Anti-p62 | Mouse | 1:500 | MBL |
| Anti-Parkin | Mouse | 1:500 | Abcam |
| Anti-Calbindin | Mouse | 1:200 | Leica |
| Anti-mouse HRP | Goat | WB 1:3000 IC 1:300 | Bio rad |
| Anti-Rabbit HRP | Goat | 1:3000 | Bio rad |
| Alexa 488-conjugated goat anti-mouse IgG | Goat | 1:1000 | Invitrogen |
| Alexa 488-conjugated donkey anti-rabbit IgG | donkey | 1:1000 | Invitrogen |
| Alexa 594-conjugated goat anti-mouse IgG | Goat | 1:1000 | Invitrogen |

(9) Immunoblot Analysis

Protein lysates were separated by SDS-PAGE and transferred to PVDF membrane. LC3-I and LCS3-II were detected by anti-LC3 antibody (Cell Signaling). The data are normalized to α-tubulin expression. The HLCs were solved in RIPA buffer and then insoluble p62 was collected as a pellet after the centrifuge of the samples.

(10) Albumin Production Analysis

Albumin production of hepatocyte-like cells were measured by Human Albumin ELISA Quantitation kit (Bethyl E80-129), according to the manufacturer's protocol. The data was normalized to Albumin-positive percentages in the samples.

(11) Cell Size Analysis

The cell sizes of albumin-positive cells was calculated by Developer Toolbox software of IN CELL ANALYZER 6000 (GE Healthcare).

(12) Indocyanine Green (ICG) Analysis

The culture cells on day 18 of differentiation were treated with 1 mg/ml ICG for 30 min at 37° C. The cells were washed three times with PBS and the positive cells were analyzed. The cells were then incubated with the medium for 5 min and were re-analyzed again.

(13) Measurement of ATP

Hepatocyte-like cells derived from the iPSC lines were cultured in DMEM medium in the absence of glucose for 24 hours and were then cultured in the DMEM medium containing 10% FBS and high glucose for 6 hours. ATP was measured by ATP measurement Kit (TOYO INK), according to the manufacturer's protocol.

(14) Mitochondria Staining by MitoTrackers

Hepatocyte-like cells derived from the iPSC lines were cultured in the presence of 100 nM MitoTracker red CMXRos (Molecular Probe) for 20 min and were analyzed by FACS. The HLCs were stained with JC-1, according to the manufacturer's protocol (Molecular Probe). The red and green fluorescence intensities of JC-1 stainings were measured by Developer Toolbox software of IN CELL ANALYZER 6000 (GE Healthcare).

(15) TUNEL Staining

TUNEL staining was performed by APO-BrdU TUNEL assay kit (Invitrogen), according to the manufactual protocol.

(16) Ammonia Removal and Urea Secretion Activities

HLCs were cultured in the medium with 1 mM ammonium chloride for two days. The supernatant was collected and then, according to the manufactual protocols, ammonia and urea concentrations were measured by ammonia assay kit (SIGMA) and urea colorimetric assay kit (BioVision), respectively.

(17) Cyclodextrins

2-Hydroxypropyl-α-cyclodextrin with an average degree of substitution of 5.0 (HPACD), 2-hydroxypropyl-β-cyclodextrin with an average degree of substitution of 4.7 (HPBCD), and 2-hydroxypropyl-γ-cyclodextrin with an average degree of substitution of 6.4 (HPGCD) were obtained from Nihon Shokuhin Kako (Tokyo, Japan).

(18) Antibody Staining and FACS Analysis

Differentiated iPS cells were harvested on day 4 and stained with biotin-conjugated mouse anti-human CXCR4 antibody (R & D Systems) and Streptoavidin-allophycocyanin (SA-APC, eBioscience). The proportion of apoptotic and dead cells was measured by flowcytometer using Annexin (Beckman Coulter) and 7-amino-actinomycin D (7-AAD, Beckman Coulter).

2. Results

Example 1: Vector Generation

By using temperature-sensitive Sendai virus (SeV) vectors, iPS cells containing the sequences for four reprogramming factors (OCT3/4, SOX2, KLF4 and c-MYC) were generated.

To increase the efficiency of iPS cell generation and reduce the length of time the vector remains inside the cells, the inventors generated a new Ts-SeVvector, TS12KOS, carrying coding sequences for three of the above factors, KLF4(K), OCT3/4(O), and SOX2(S) tandemly linked in the KOS direction (FIG. 1). The TS12KOS vector contains three mutations that produce alanine residues (D433A, R434A, and K437A) in the large protein(L)-binding domain of the phosphoprotein, a component of SeV RNA polymerase. SeV carrying these three mutations showed moderate expression of GFP at 37° C., but weak expression at temperatures above 38° C.

Example 2: iPS Cell Generation with SeV Vector

Fibroblasts from healthy volunteers and patients were generated and isolated from explants of skin biopsy following informed consent under protocols approved by the ethics committee assigning inventors. Skin samples were minced and cultured in Dulbecco's modified essential medium (DMEM, Life technologies) supplemented with 10% Fetal Bovine Serum (FBS). After the fibroblast appeared, it was expanded for iPS cell induction.

To generate iPS cells from peripheral blood cells, mononuclear cells (MNCs) were isolated by Ficall gradient. To stimulate T lymphocytes, MNCs were cultured on anti-CD3 antibody-coated dishes with IL-2 for five days.

iPS cells were generated from human skin-derived fibroblasts and stimulated T lymphocytes as described in the report by Seki (2010, non-patent document 3). Briefly, $1 \times 10^5$ of human MNCs per well of 48-well plate and $5 \times 10^5$ cells of human fibroblast cells per well of 6-well plate were seeded one day before infection and then were infected with Sendai virus (SeV) vectors at various multiplicity of infection (MOI) including three, ten and thirty. After two-day culturing for blood cells and seven-day culturing for fibroblasts, the cells infected were harvested by trypsin and re-plated at $5 \times 10^4$ cells per 60 mm dish on the mitomycin C (MMC)-treated mouse embryonic fibroblast (MEF) feeder cells. Next day, the medium was replaced in human iPS cell medium. The cultures with new Sendai virus infection were incubated at 36° C. for one week. From 18 to 25 days after infection, colonies were picked up and re-cultured again in human iPS cell medium. To remove Sendai virus, the temperature of culture shifts from 37° C. to 38° C. at passage 1 or 2 of iPS cells.

Figure 2:
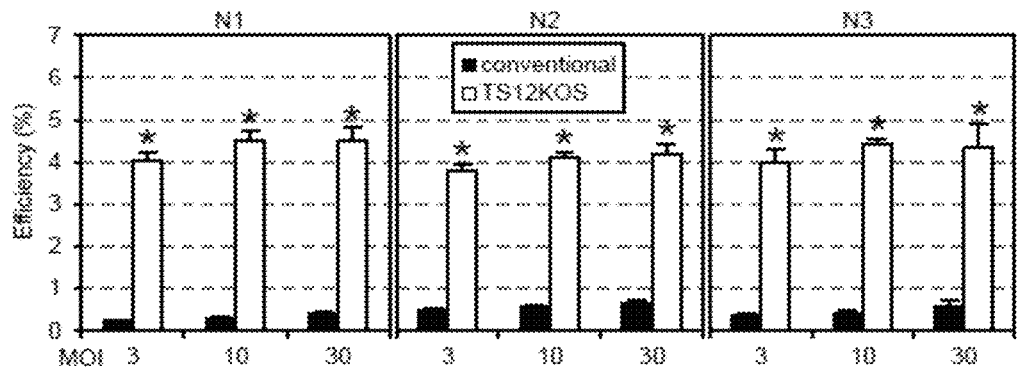
FIG. 2 It shows iPS cell generation from human skin-derived fibroblasts. N1, N2, and N3 indicate individual healthy volunteers. Experiments were conducted in triplicate (mean±SD). *P<0.01, TS12KOS vector versus conventional vector, Student's t-test.

First, the TS12KOS and conventional SeV vectors in terms of the efficiency of iPS cell generation from human skin fibroblasts of healthy volunteers was compared (FIG. 2). On day 28 after induction, the number of colonies with alkaline phosphatase (AP)-positive staining and human embryonic stem (ES) cell-like morphology were counted. The efficiency of iPS cell generation was significantly higher using the TS12KOS vector than with the conventional vector.

Figure 3:
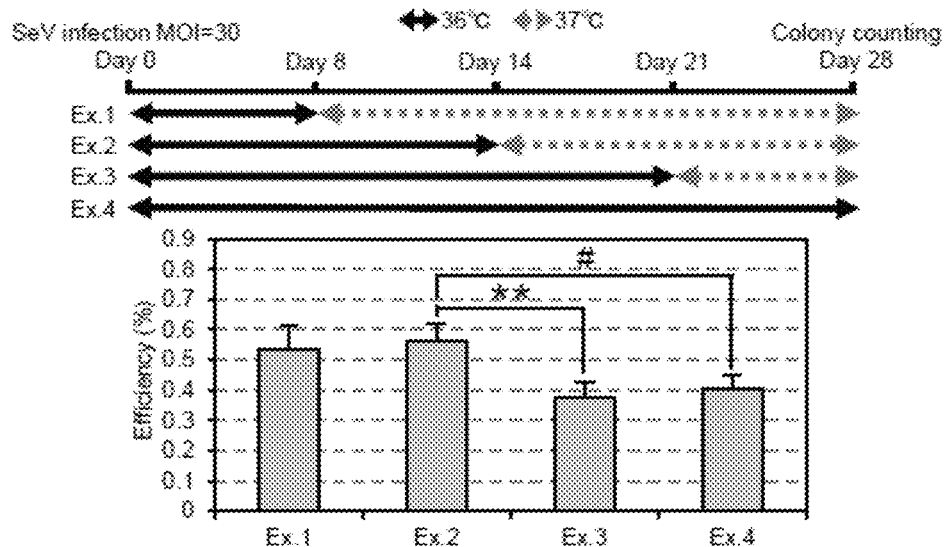
FIG. 3 It shows temperature shift from 37° C. to 36° C. for the indicated periods in iPS cell generation. Data are means±SD of three independent experiments. **P<0.02, #P<0.05, Student's t-test.

Next, the effect of temperature shift on iPS cell generation from human fibroblasts was examined. When the culture temperature was shifted from 37° C. to 36° C. for the initial two weeks after infection, the efficiency of colony formation remained high, and however, when the temperature downshift continued for three weeks or more after infection, the efficiency decreased significantly (FIG. 3). Temperature shift for the initial one week and two week is more effective than for later period. Therefore, a temperature downshift for the initial one week only was used in the following experiments.

Example 3: Analysis of Established iPS Cells

Nested RT-PCR analysis of viral RNA was conducted to determine whether the TS12KOS vector was eliminated from the iPS cells earlier than the conventional SeV vector. The individual colonies were expanded and the temperature was shifted from 37° C. to 38° C. for 3 days at various passages. In conventional SeV infection, temperature upshifts at passage 1 or 2 induced no virus removal. In contrast, in the case of the TS12KOS vector, when the temperature was upshifted at passage 1 and 2, 84% and 65%, respectively, of iPS cell-like clones were negative for the viral genome (FIG. 4). These results indicate that the TS12KOS vector was superior to the conventional SeV vector in terms of both the efficiency of iPS cell generation and the removal of virus from iPS cells.

Example 4: iPS Cell Generation from Human Peripheral Blood Cells

One goal is to develop safe and efficient vectors to generate iPS cells from human peripheral blood cells. Peripheral T lymphocytes were stimulated with both anti-CD3 antibody and interleukin 2, and then were infected with SeV vectors to generate iPS cells. The generation of iPS cells was significantly more efficient using the TS12KOS vector than with the conventional SeV vector (FIG. 5A). In conventional SeV infection, temperature shifts from 37° C. to 38° C. at passage 1 and 2 induced no elimination from the iPSC clones. In contrast, when TS12KOS vector was used under the same conditions, 65% and 47%, respectively, of the clones were negative for the viral genome (FIG. 5B). Therefore, similar to the results obtained with fibroblasts, the elimination of TS12KOS vector from iPS-like cells derived from peripheral T lymphoctyes was faster than that observed for conventional SeV vector.

The colonies formed from skin fibroblasts and peripheral blood cells induced by TS12KOS vector exhibited a typically ES cell-like morphology and expressed a set of typical markers for pluripotency (data not shown). These iPS cell lines had a normal 46 XY karyotype even after the temperature upshift and culturing for more than 10 passages (data not shown). To confirm the pluripotency of the clonal lines, a single cell line was transplanted into the testis of immunodeficient mice. Twelve weeks after injection, the iPS cell line tested formed a teratoma that contained derivatives of all three germ layers (FIG. 6). That is, the iPS cell lines generated with the TS12KOS vector meet the criteria of iPS cells.

Example 5: Establishment of iPS Cells Expressing Disease Phenotype

Figure 7:
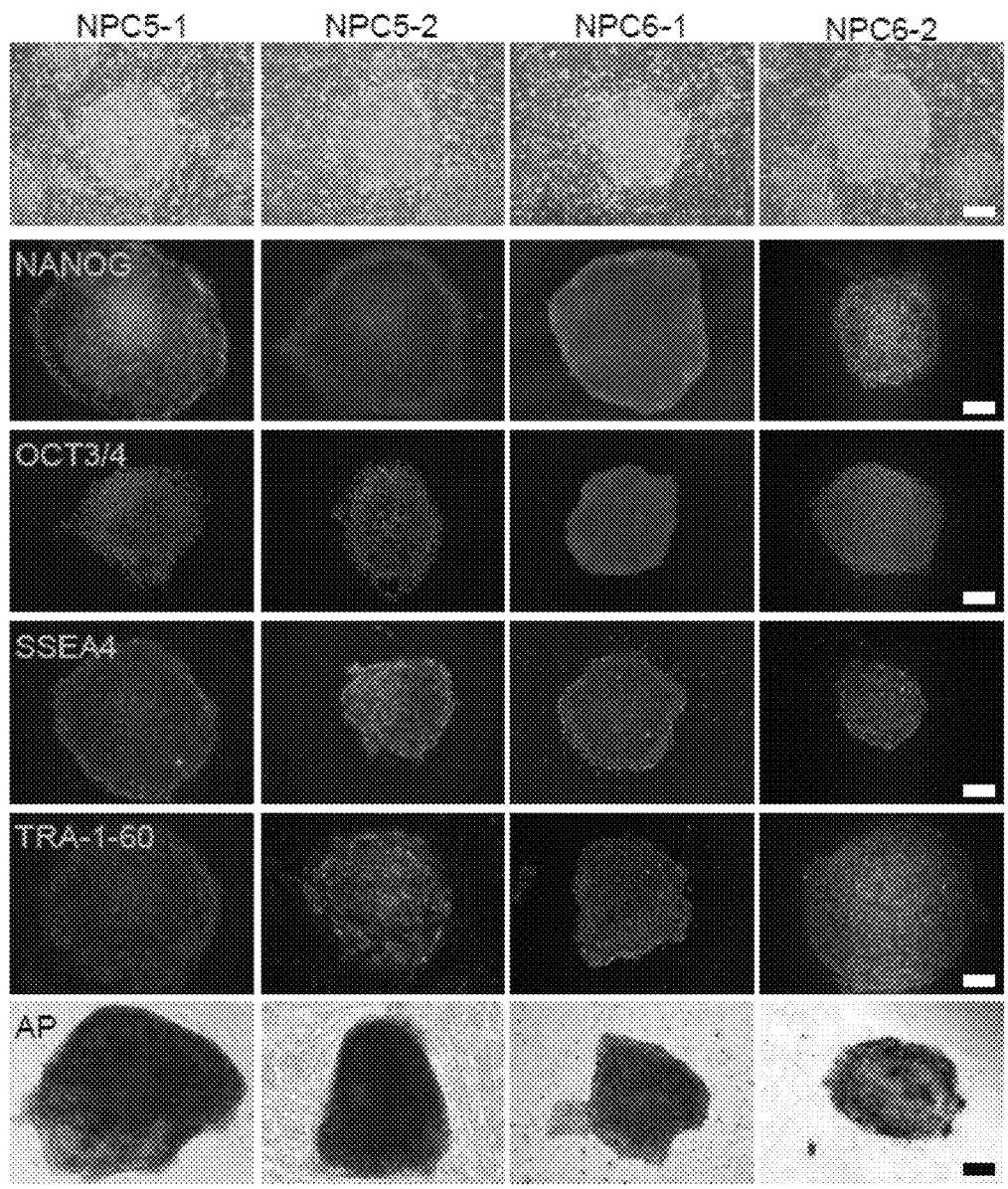
FIG. 7 It shows phase contrast images of iPSC lines derived from the NPC patients as immunofluorescence and alkaline phosphatase (AP) staining. The iPSC lines NPC5-1 and -2, and NPC6-1 and -2, were derived from the NPC patients, NPC5 and NPC6, respectively. Scale bars, 200 μm.
Figure 8:
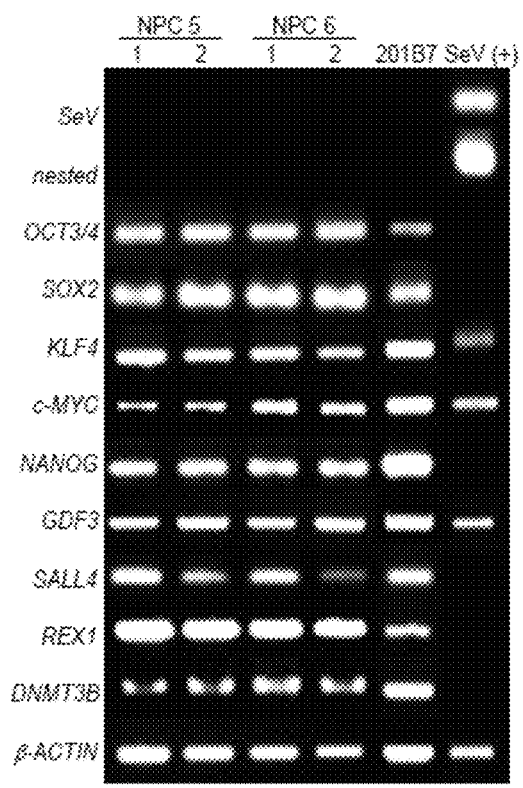
FIG. 8 It shows RT-PCR analysis of Sendai virus and human ES-cell markers of iPSC lines derived from the NPC patients. NPC5 and NPC6 were derived from the NPC patients, NPC5and NPC6, respectively. 201B7, control human iPSC line; SeV(+), Day 7 SeV-infected human fibroblasts; SeV, first RT-PCR for SeV; Nested, nested RT-PCR for SeV.

To explore the use of disease-derived iPS cells as cellular models, inventors focused on Niemann-Pick disease type C (NPC), which is a lysosomal storage disease associated with mutations in the NPC1 and NPC2 genes. Npc1 acts as a transporter between endosomes and lysosomes, and Npc2 works cooperatively with Npc1 to transport molecules in the cell. Mutations in the NPC1 and NPC2 genes disrupt this transporting system, resulting in the accumulation of free cholesterol and glycolipids in lysosomes. By using the TS12KOS vector, iPS cell lines were established from skin fibroblasts of two patients carrying different NPC1 mutations. The efficiency of iPS cell generation from these patients was similar to that from healthy volunteers. The NPC-derived iPS cell lines exhibited ES cell-like morphology (FIG. 7) and expressed a set of pluripotent markers (FIG. 8). Nested RT-PCR analysis determined that the iPS cell lines were negative for SeV (FIG. 8).

Figure 9:
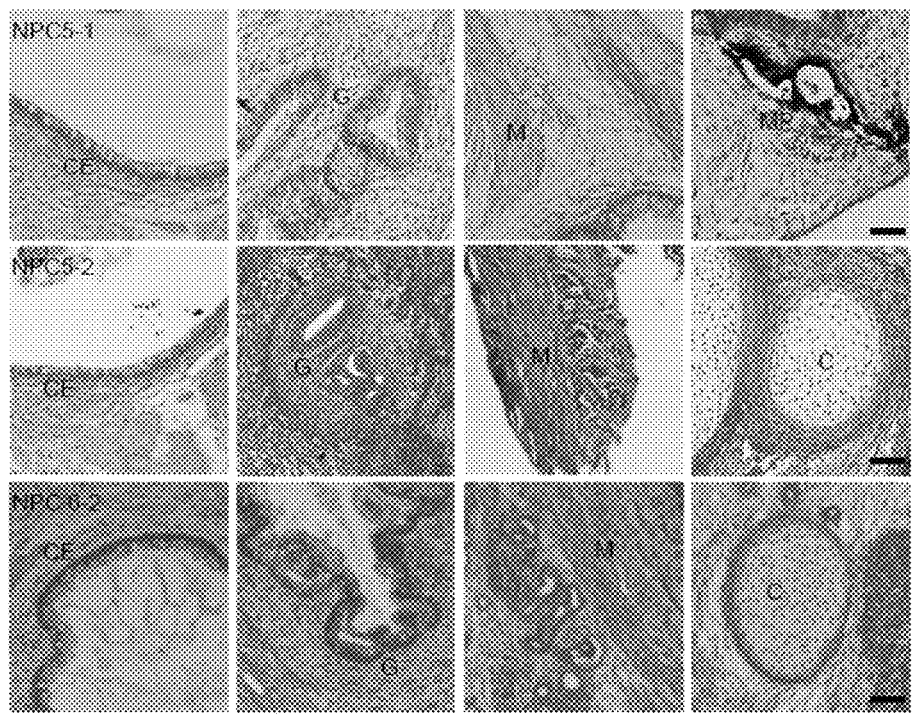
FIG. 9 It shows Histological analysis of NPC-iPSC-derived teratomas after hematoxylin and eosin staining. CE, cuboidal epithelium (ectoderm); G, glandular structure (endoderm); M, muscle tissue (mesoderm); C, cartilage (mesoderm); MP, melanin pigment (ectoderm). Scale bars, 100 μm.
Figure 10:
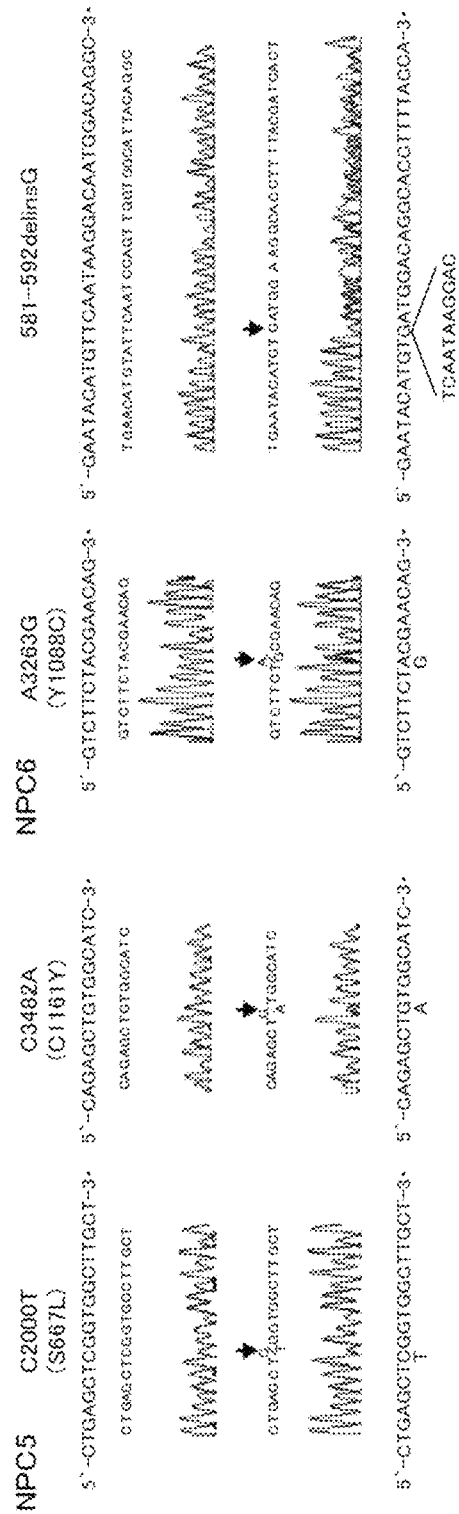
FIG. 10 It shows mutations in the NPC1 gene of NPC-derived iPSC lines. The mutations 2000C>T (S667L) and 3482G>A (C1161L) were observed in iPSC lines derived from patient NPC5 (leftpanel), whereas iPSC lines derived from patient NPC6 carried both 3263A>G (Y1088C) and a short deletion mutation in which the nucleotide region from 581 to 592 was replaced by a G residue, resulting in a frame shift (rightpanel). Mutations are indicated by arrows.

Next, the differentiation potential of the NPC-derived iPS cell lines was investigated by evaluating teratoma formation. Histological analysis revealed that the teratomas analyzed consisted of the descendants of all three germ cell layers such as cuboidal epithelia, melanin pigment, cartilage, muscle, and various glandular structures (FIG. 9). The established iPS cell lines had a normal karyotype, 46XY and 46XX (data not shown). Mutations in the NPC1 gene were confirmed by DNA sequencing (FIG. 10). Thus the NPC-derived iPSC lines fulfilled the criteria for iPS cells.

Example 6: Analyses of NPC-Derived iPSClines

Figure 11:
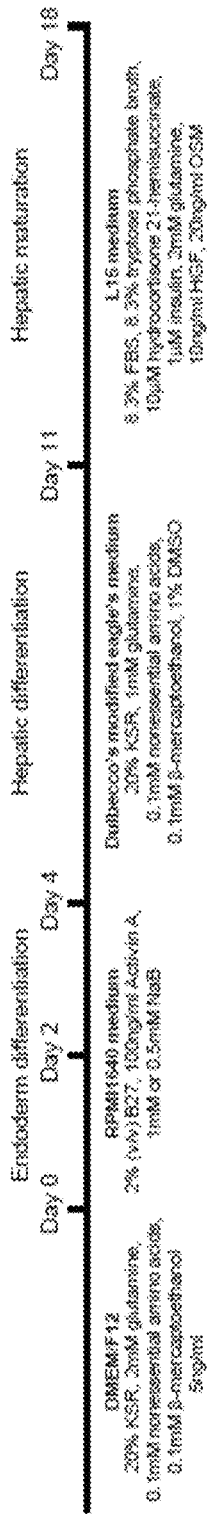
FIG. 11 It shows a pathway of iPS cell differentiation into hepatocyte-like cells. The pathway is divided into three periods: endoderm differentiation from day 0 to day 4, hepatic differentiation from day 4 to day 11 and hepatic maturation from day 11 to day 18. The culture conditions are described below each period. The cells were harvested on both day 4 and day 11 and reseeded under the next conditions.
Figure 12:
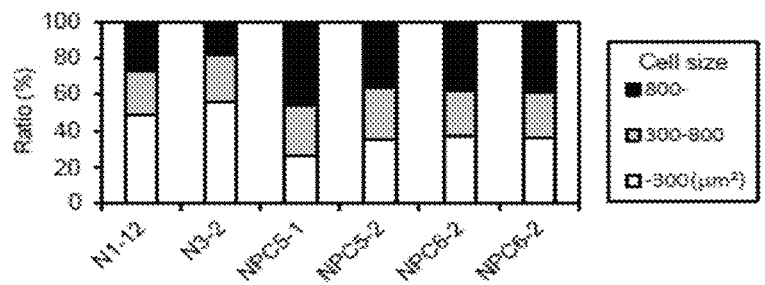
FIG. 12 It shows cell size of HLCs derived from NPC-iPSC lines.
Figure 13:
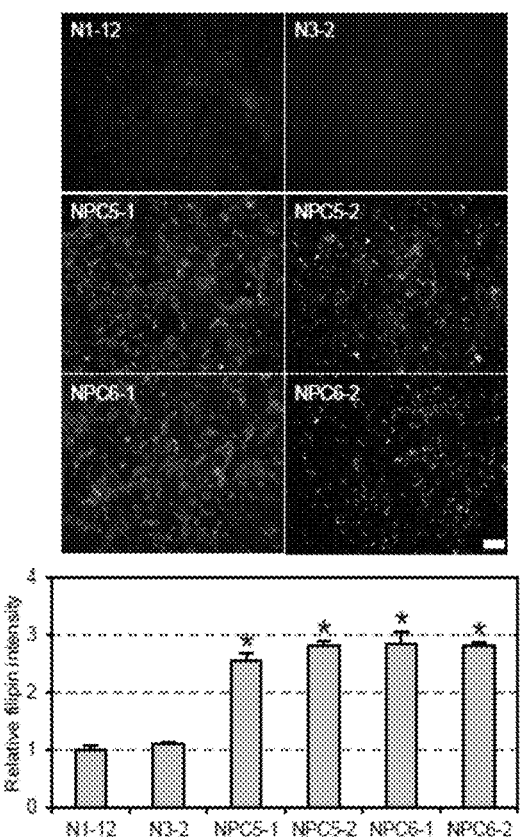
FIG. 13 It shows cholesterol accumulation in HLCs derived from NPC-iPSC lines. Free cholesterol was examined by filipin staining (upper panel), and the relative intensity was calculated relative to the normal iPSC line, N1-12 (lower graph). Data are means±SD of three independent experiments. *$P<0.01$, the indicated NPC-iPSC line versus the normal iPSC lines, Student's t-test. Scale bars, 100 μm.

Enlargement of the liver is one of major symptoms of NPC patients, and those with severe forms of the disease suffer from liver dysfunction and failure. To investigate the effect of Npc1 deficiency on the hepatocytic lineage, NPC-derived iPSC lines were differentiated into hepatocyte-like cells expressing albumin. In a previous study, treatment with Activin A selectively induces the differentiation of mouse ES cells into definitive endoderm cells and hepatocyte-like cells (HLCs), and an endodermal surface marker, Cxcr4, could be used to detect endodermal differentiation. Here, based on these results, culture conditions were modified, in which modified conditions HLCs were easily generated from human iPS cells (FIG. 11). On day 18 of differentiation, the HLCs expressed α-fetoprotein (~65% of total cells) and albumin (~80% of total cells) and other hepatic makers (data not shown), and they absorbed indocyanine green (ICG) and stored glycogen (data not shown). The generation rate of definitive endoderm-like cells, calculated as the percentage of Cxcr4-positive cells, and the efficiency of hepatic differentiation, calculated from the percentage of albumin-positive cells and the marker expressions, were similar between the normal iPS cell and the NPC-derived iPS cell lines. In contrast, the cell size of NPC-derived HLCs was larger than that of control HLCs (FIG. 12). In NPC patients, defective transportation of lipids from endosomes to lysosomes results in the accumulation of free cholesterol in lysosomes. Therefore, to detect free cholesterol in the cells and thus assess the level of cholesterol accumulation, filipin staining was performed. Negligible numbers of positively stained cells were observed in the control HLCs derived from healthy volunteers. In contrast, extreme levels of cholesterol accumulation were detected in the NPC-derived HLCs (FIG. 13), which suggests that these cells mirror the cellular phenotype of NPC.

Figure 14:
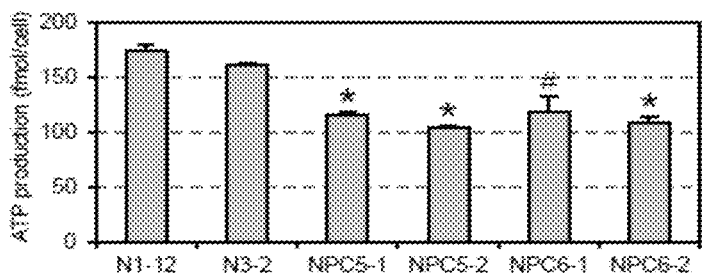
FIG. 14 It shows ATP levels in HLCs derived from iPSC lines. Experiments were conducted in triplicate (mean±SD). *$P<0.01$, #$P<0.05$, the indicated NPC-iPSC line versus the normal iPSC lines, Student's t-test.
Figure 15:
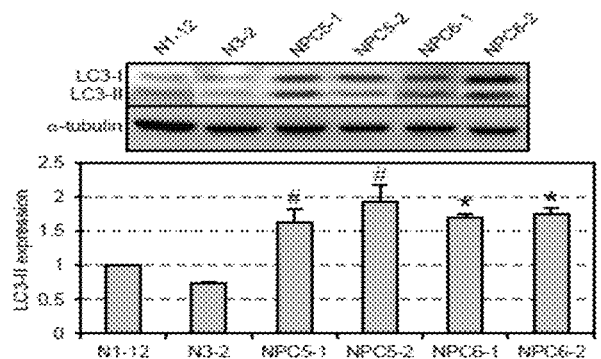
FIG. 15 It shows expression level of microtubule-associated protein 1 light chain 3 (LC3). *$P<0.01$, #$P<0.05$, the indicated NPC-iPSC lines versus the normal iPSC lines, N1-12 and N3-2, Student's t-test. The expression level was normalized to the expression of a-tubulin in each iPSC line.
Figure 16:
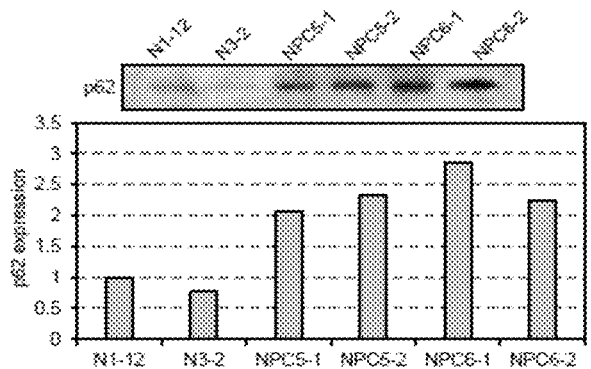
FIG. 16 It shows expression level of insoluble form of p62.
Figure 17:
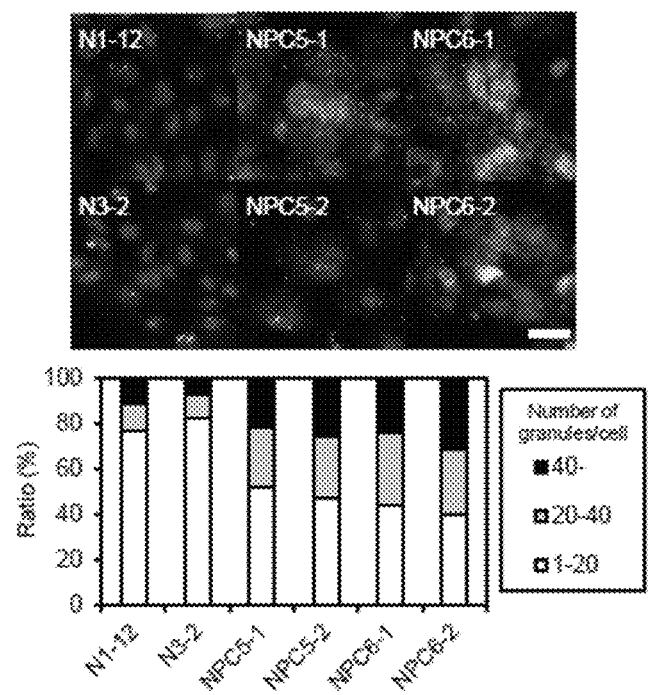
FIG. 17 It shows immunofluorescence staining for p62. Abnormal aggregation of p62 was strongly present in NPC-derived HLCs (upper panel). The aggregated granules were counted and the results summarized in the lower graph. The proportion of cells carrying more than 40 granules was increased in NPC-derived HLCs comparing to normal HLCs. Nuclear staining, Hoechst 33258; Scale bars, 25 μm.

Next, the various functions of HLCs derived from normal iPS cell and NPC-iPS cell lines were investigated. There was not detection in any differences in terms of ICG uptake or release, glycogen storage, albumin production, urea secretion, or ammonia removal, all of which are indicative of hepatocyte function (data not shown). The ATP levels in NPC-HLCs were significantly lower than those in control HLCs (FIG. 14). Despite this, apoptosis in the NPC-HLCs was not exacerbated compared to that in the controls (date not shown). To investigate the membrane potential of mitochondria, the specific MitoTracker staining reagents, JC-1 and CMXRos were used. JC-1 concentrates in the mitochondria and aggregates at normal mitochondrial membrane potentials, resulting in a high red/green fluorescence intensity ratio. A reduction in the mitochondrial membrane potential affects the aggregation of JC-1, resulting in a decreased red/green fluorescence intensity ratio. In addition, CMXRos accumulates in mitochondria at normal membrane potential. There was no detection in any difference in staining patterns for JC-1 or CMXRos between normal and NPC-derived HLCs (data not Cellular autophagy is impaired in lysosomal storage diseases. The autophagy pathway in control and NPC-derived HLCs were monitored by using two methods. First expression of microtubule-associated protein 1 light chain 3 (LC3), which is a marker protein for autophagy, was examined. C-terminal processing of LC3 produces LC-I, which is modified to LC-II with the initiation of autophagosome formation. Then, p62/SQSTM1 (p62) expression was measured to assess autophagic flux. Because p62 binds to LC3 and is degraded upon fusion with the lysosome, impairment of autophagy flux results in the accumulation and aggregation of insoluble p62. The expression levels of LC3-II and insoluble p62 proteins were higher in NPC-HLCs than in normal HLCs (FIGS. 15 and 16). In addition, excessive p62 aggregation was observed in NPC-derived HLCs compared with normal HLCs (FIG. 17). These results suggest that autophagy was upregulated in the NPC-derived HLCs and autophagic flux was impaired in the NPC-derived HLCs.

Example 7: Effect of Various Cyclodextrin Treatments on Cholesterol Accumulation and Restoration of Cellular Functions Because NPC-derived iPS cell lines expresses phenotype of NPC, as described above, the present invention provides an in vitro system for screening drug candidates for NPC treatment. Since extreme cholesterol accumulation in NPC iPS cell-derived HLCs was observed, it enables to examine the effect of various drug treatments on this process.

Figure 18:
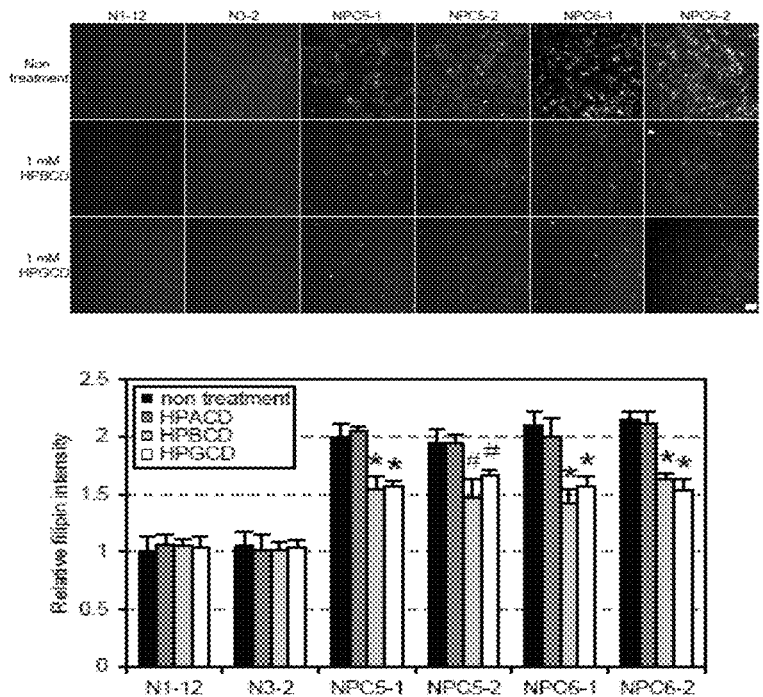
FIG. 18 It shows effect of a series of hydroxypropyl-cyclodextrins on the reduction of free cholesterol accumulation in NPC-derived HLCs. The upper panel shows the results of filipin stained, and the lower panel shows a result analyzed with an IN CELL ANALYZER. Data are mean±SD of three independent experiments. *$P<0.01$, #$P<0.05$, non-treatment versus treatment of each NPC-derived HLC, Student's t-test. Scale bars, 50 μm.

It has been reported that 2-Hydroxypropyl-β-cyclodextrin (HPBCD) is effective for reducing of cholesterol accumulation in NPC1-defective cells. The inventors therefore treated the HLCs derived from normal and NPC-iPS cell lines with a series of 2-hydroxypropyl-cyclodextrins with different cavity sizes, and observed effect of a series of hydroxypropyl-cyclodextrins. HLCs were cultured with 1 mM of the indicated hydroxypropyl-cyclodextrin for 4 days, stained with filipin and analyzed with an IN CELL ANALYSER (GE Healthcare) (FIG. 18). In the experiment using NPC-HLCs of the present invention, the observed cholesterol accumulation was significantly decreased with HPBCD treatment. Interestingly, 2-Hydroxypropyl-α-cyclodextrin (HPACD) did not show any effect on cholesterol accumulation, whereas 2-Hydroxypropyl-γ-cyclodextrin (HPGCD) reduced the cholesterol accumulation in NPC-HLCs to the same extent as that observed for HPBCD.

Figure 19:
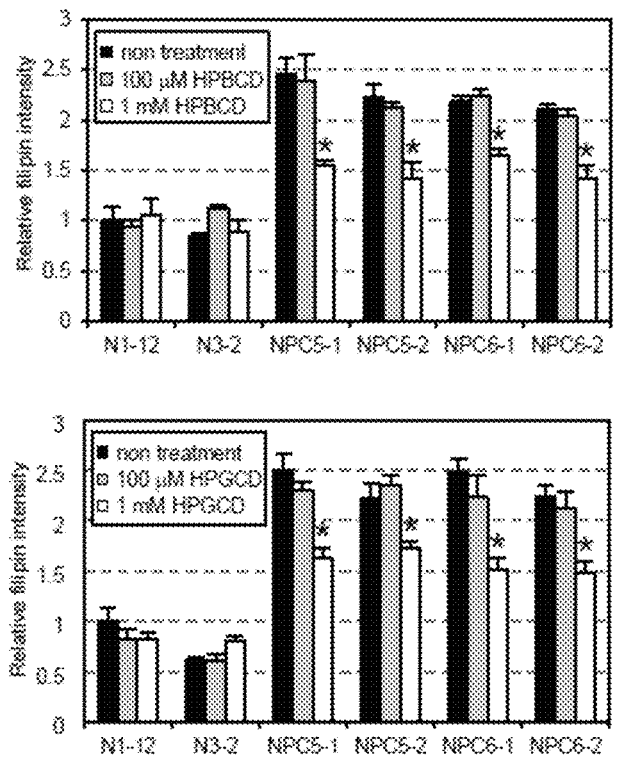
FIG. 19 It shows dose effect of HPBCD and HPGCD on the reduction of free cholesterol accumulation in NPC-derived HLCs. *$P<0.01$, non-treatment versus treatment of each NPC-derived HLC, Student's t-test.
Figure 20:
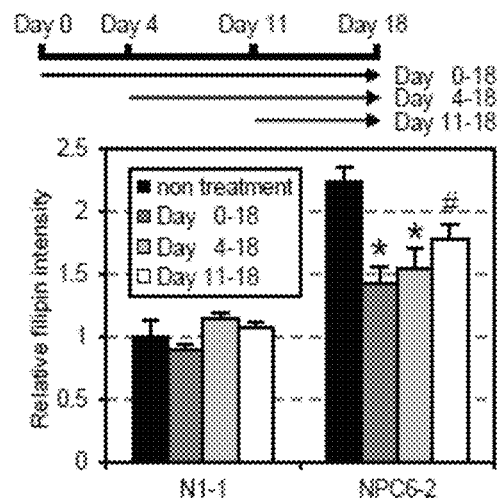
FIG. 20 It shows effect of HPBCD on the reduction of free cholesterol accumulation in NPC-derived iPS cell differentiation. The upper panel shows experimental design and the lower graph shows filipin staining. Experiments were conducted in triplicate(mean±SD). *$P<0.01$, #$P<0.05$, non-treatment versus treatment, Student's t-test.

The size of HLCs is decreased by the treatments with HPBCD and HPGCD (data not shown). Effects of various concentration of HPBCD and HPGCD in NPC-derived HLCs was observes. HLCs were cultured with HPBCD or HPGCD for 4 days, stained with filipin and analyzed with an IN CELL ANALYSER (GE Healthcare). Low concentrations (100 μM) of HPBCD and HPGCD were ineffective for reducing cholesterol accumulation (FIG. 19). We next treated the cells during HLC differentiation with HPBCD, which was effective at the intermediate stages in hepatic differentiation (FIG. 20).

Figure 21:
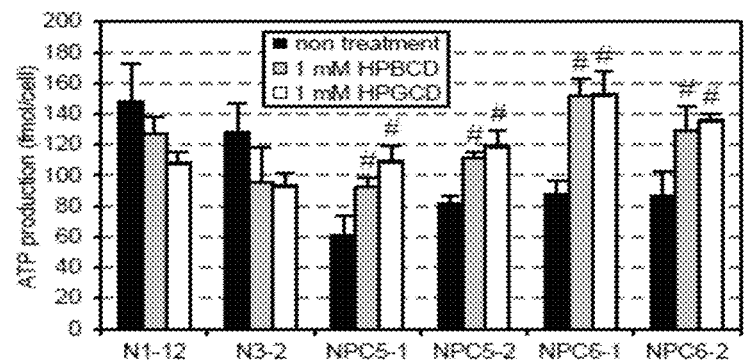
FIG. 21 It shows effects of hydroxypropyl-cyclodextrin (HPCD) treatments on ATP levels of HLCs derived from NPC-iPSC lines. Data are mean±SD of three independent experiments. #$P<0.05$, non-treatment versus treatment, Student's t-test.
Figure 22:
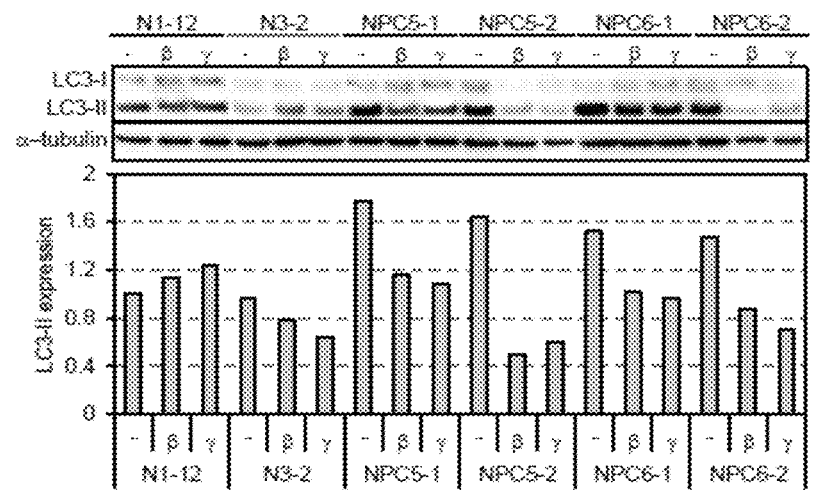
FIG. 22 It shows effects of HPCD treatments on expression level of LC3 in NPC-derived HLCs. β: Treatment with 1 mM HPBCD for four days; γ: 1 mM HPGCD treatment for four days. The expression level was normalized to α-tubulin expression in each iPS cell line.
Figure 23:
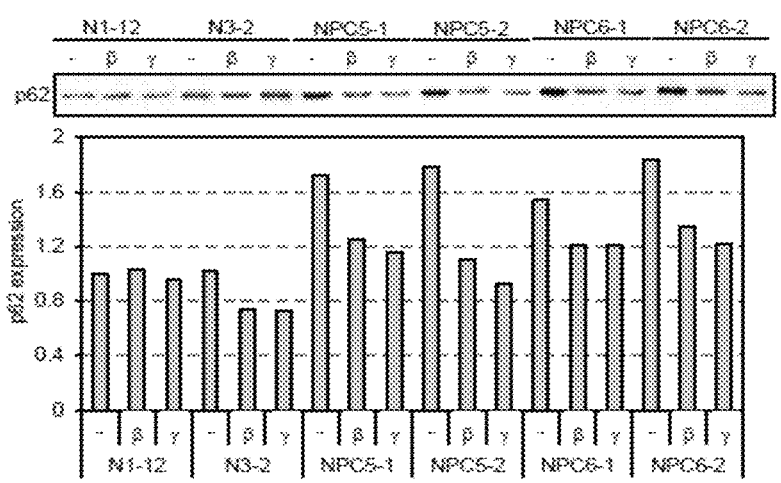
FIG. 23 It shows effects of HPCD treatments on p62 expression level in NPC-derived HLCs FIG. 24 It shows the proportion of NPC-derived HLCs carrying insoluble p62 aggregation with HPCD treatments. β: Treatment with 1 mM HPBCD for four days; γ: 1 mM HPGCD treatment for four days.
Figure 24:
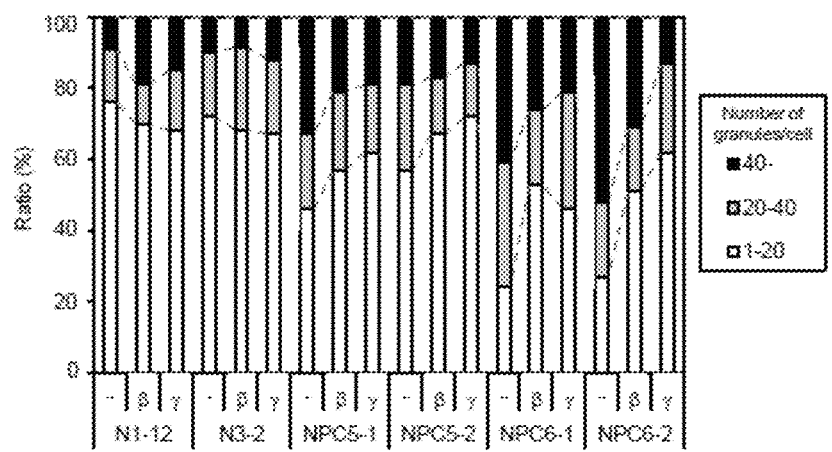

Because the NPC-derived HLCs exhibited abnormally low ATP levels and abnormal autophagy, the inventors examined whether cyclodextrin treatment could restore these abnormalities. HLCs were culture with 1 mM 2-hydroxypropylcyclodextrins (HPCDs) for 4 days, and ATP level, expression levels of LC3 and p62, and insoluble p62 granules were measured. The results showed that treatments with HPBCD and HPGCD recovered both the ATP level (FIG. 21) and the autophagy function (FIGS. 22-24). As shown in FIG. 22, the expression level of LC3 was recovered to normal levels by treatments with HPBCD and HPGCD, which suggest that the treatments restored the abnormal induction of autophagy. As shown in FIG. 23, HPBCD and HPGCD treatments reduced the amount of insoluble p62. Also, as shown in FIG. 24, the proportion of HLCs carrying more than 40 granules of insoluble p62 aggregation was greatly reduced by HPBCD and HPGCD treatments. These suggest that the treatment restored the impairment of autophagic flux. These suggest that NPC-iPS derived HLCs are useful for evaluating a drug candidate. These also suggest that HPGCD, in addition to HPBCD, is a promising drug candidate for NPC treatment.

Example 8: Effects of HPBCD and HPGCD on NPC-Derived HLCs

Microarray analysis for HLCs treated with HPBCD or HPGCD, cluster analysis and principal component analysis (PCA) were conducted to evaluate whether the effect, which are ATP level restoration and autophagy function restoration, of HPBCD on HPLCs is the same mechanism of action as that of HPGCD. The HLCs induced by the procedure described in Example 11 were cultured in a medium supplemented with HPBCD or HPGCD for 4 days. The control HLCs were cultured in the absence of HPCDs. RNA was extracted from HLCs for exhaustive gene expression analysis using microarray analysis. The procedures are described below.

Two hundred fifty ng of total RNA from the iPSC-derived HLCs cultured in each condition were labeled with biotin and fragmented according to the manufacturer's protocol (3' IVT Express kit, Affymetrix). Then, samples were hybridized to a GeneChip® Human Genome U133 Plus 2.0 (Affymetrix). Arrays were scanned with a GeneChip® Scanner 3000(Affymetrix). Data were analyzed using GeneSpring GX 12.5 software (Agilent technologies). Each chip is normalized to the median of the measurements. The genes with fold change >1.5 were considered to be differentially expressed genes between NPC and normal HLCs. Comparing the profiles of differentially expressing genes each other revealed commonly up-regulated and down-regulated genes of NPC-derived HLCs. In the commonly up- or down-regulated genes, Gene set enrichment analysis (GSEA, BROADINSTITUTE) enriched the biological processes of gene ontology, which significantly contain the commonly up-regulated or down-regulated genes in NPC-derived HLCs. In the commonly up- or down-regulated genes, GSEA also enriched the biological processes of gene ontology, which contain differentially expressing genes between HPBCD and HPGCD treatments. The number of permutation was conducted one thousand times for the statistics analysis and the algorism used enriched the biological processes of gene ontology, which contain the genes that appeared in more than five times. The biological processes of gene ontology were selected and described solely based on p-value ranking. The biological processes with p value <0.05 or <0.1 were considered to be significantly altered in NPC or HPGCD treatment, comparing to normal or HPBCD treatment, respectively. Then with the hierarchical clustering analysis the genes which were significantly in the biological processes were identified.

Figure 25:
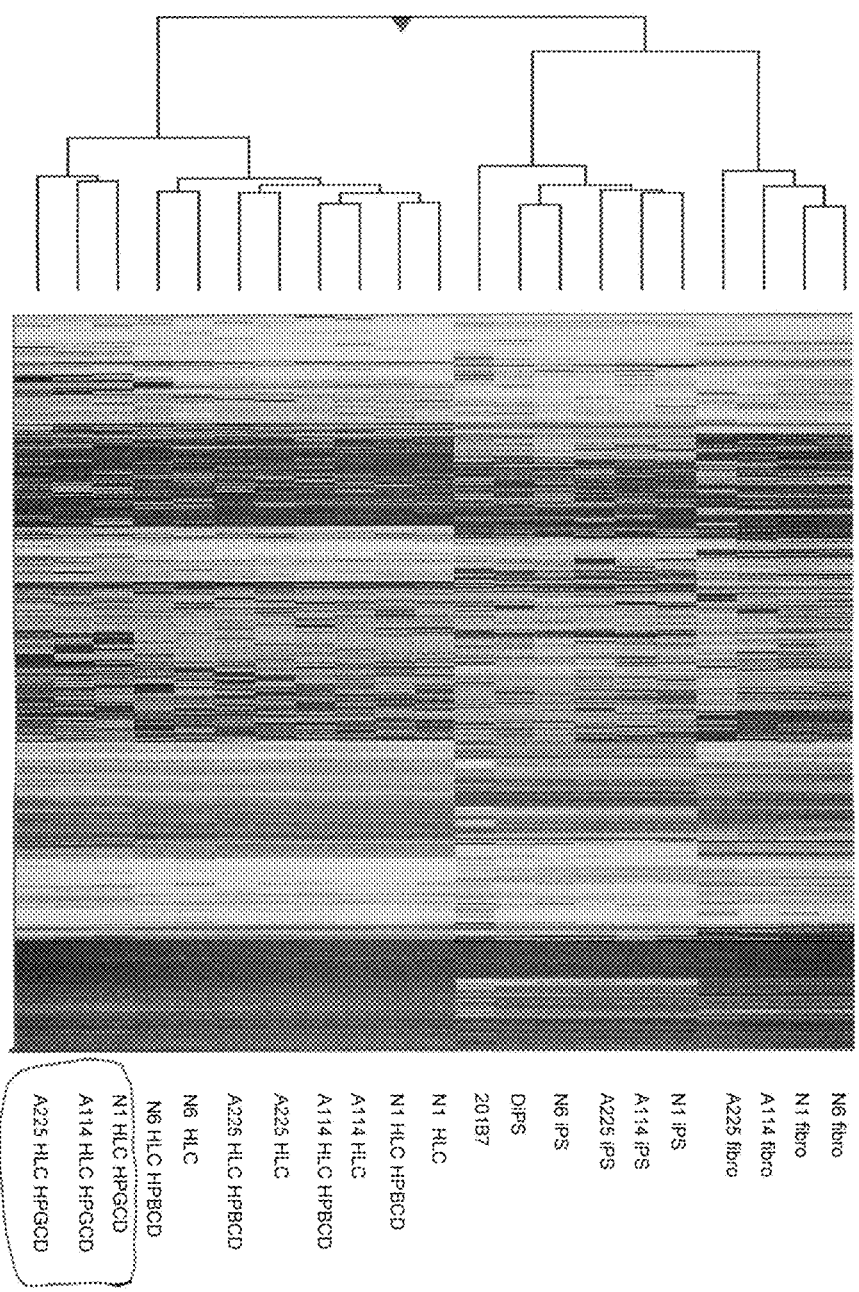
FIG. 25 It shows hierarchical clustering of genes of NPC-iPSC derived HLCs with HPCD treatments.
Figure 26:
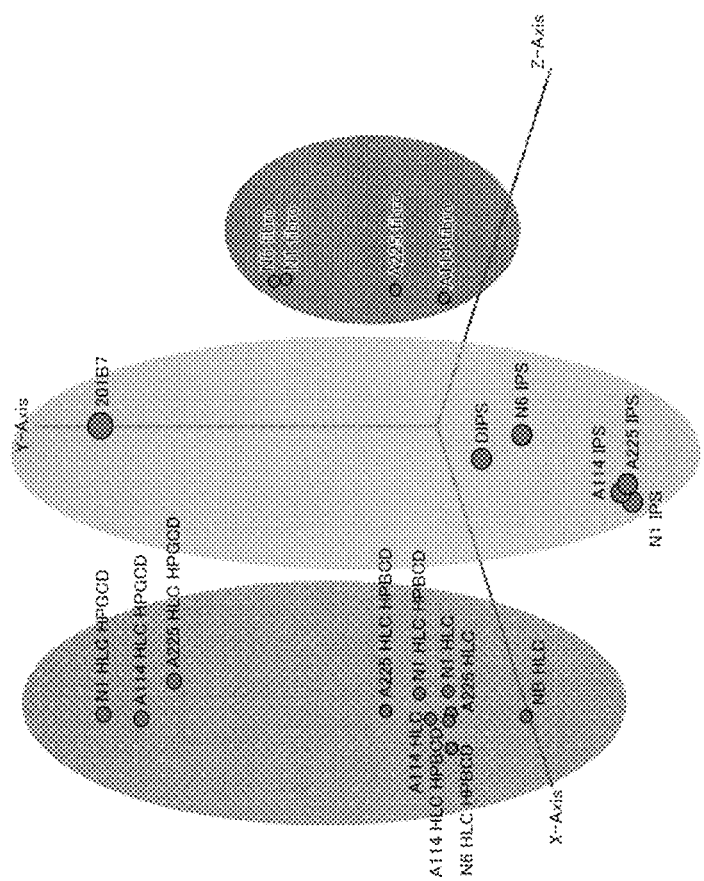
FIG. 26 It shows principal component analysis (PCA) of NPC-iPSC derived HLCs with HPCD treatments.

Each cells, including fibroblast cells (fibro) and iPS cells derived from normal volunteer (N1), patient NPC-5 (A114) and patient NPC-6 (A225) and HLCs derived those iPS cells, in the absence of HPCDs or the presence of HPBCD or HPGCD were analyzed by cluster analysis and PCA analysis. The results of cluster analysis and PCA analysis are shown in FIG. 25 or 26, respectively. It concluded that HPGCD acts with the mechanism different from HPBCD.

Figure 27:
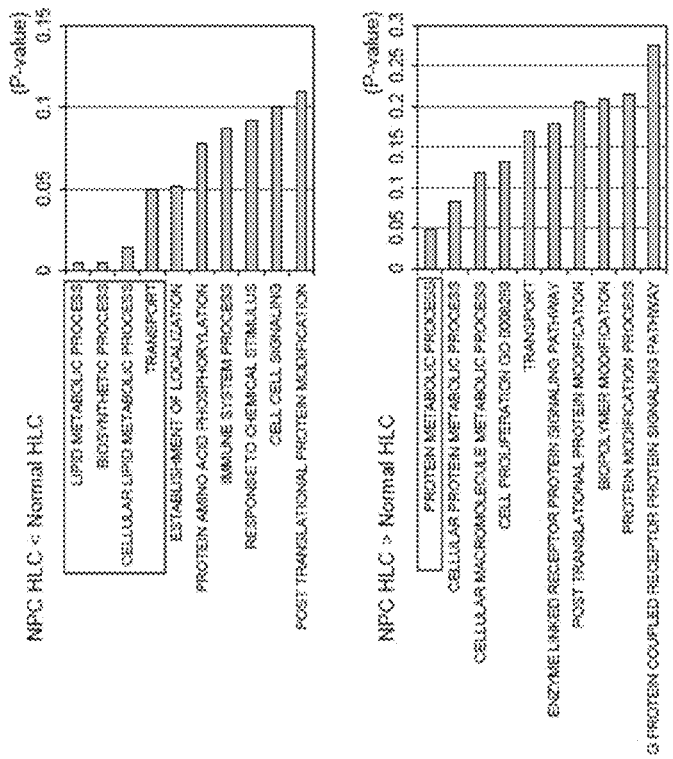
FIG. 27 It shows microarray analysis/molecular signatures in healthy donor-derived HLCs and NPC-derived HLCs. The molecular signatures enclosed in squares shows signatures significantly ($P<0.05$) changed in NPC-derived HLCs, compared to healthy donor-derived HLCs. Upper panel: downregulated signatures in NPC, lower panel: upregulated signatures in NPC.

Molecular signatures identified by the above analysis are shown in FIG. 27. The molecular signatures significantly down-regulated in NPC are shown in the upper panel and those significantly up-regulated in NPC are shown in the lower panel.

Figure 28:
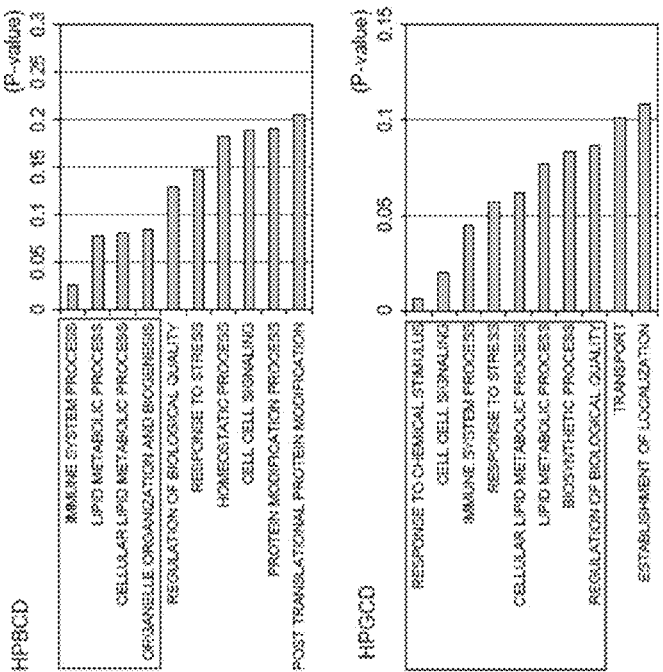
FIG. 28 It shows microarray analysis/molecular signatures with HPCBD and HPGCD treatments. Upper panel: HPBCD treatment, lower panel: HPGCD treatment. The molecular signatures enclosed in squares shows signatures significantly ($P<0.05$) changed in HPCBD and HPGCD treatments.

Expressions of the molecular signatures identified above were measured with HPBCD or HPGCD treatments. The results are shown in FIG. 28. The effect of HPBCD treatment is shown in the upper panel, and that of HPGCD is shown in the lower panel.

Figure 29:
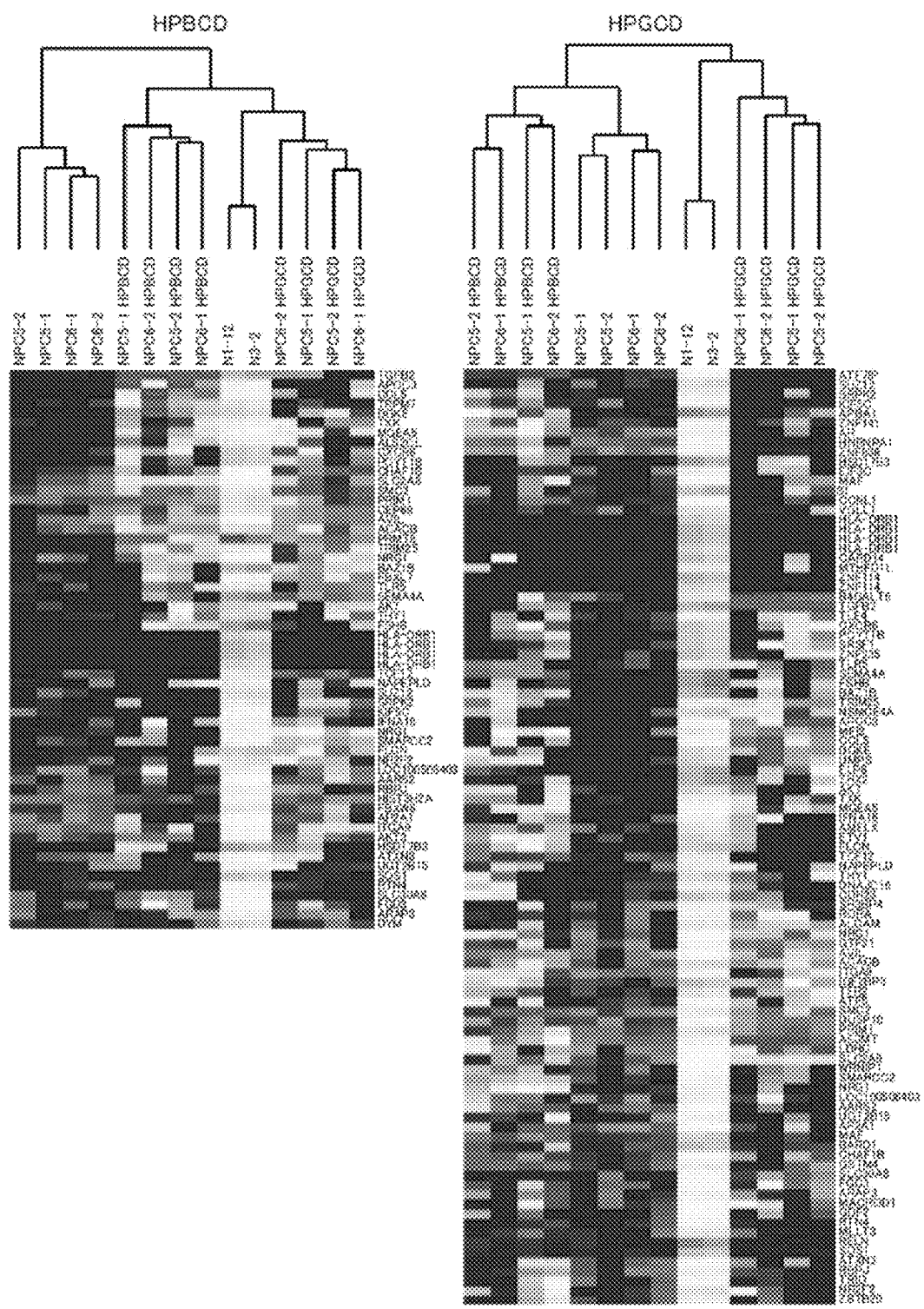
FIG. 29 It shows hierarchical clustering of genes significantly altered with HPBCD and HPGCD treatments. Left panel: genes included in the molecular signature altered with HPBCD treatment, right panel: genes included in the molecular signature altered with HPGCD treatment.

Hierarchical clustering of genes significantly altered with HPBCD and HPGCD treatments were measured. The results are shown in FIG. 29. The data sets of the genes included in the molecular signatures, as shown in the red squares of FIG. 28, were clustered according to Euclidean distance metrics. The gene expression patterns of the molecular signature altered with HPGCD treatment were closer to that of normal HLCs than those with HPBCD treatments.

Example 9: Effects of HPGCD Treatment Using NPC-Model Mouse

Effects of HPGCD treatment on cholesterol accumulation in NPC-derived HLCs were evaluated using NPC-model mice. NPC model mice bear a spontaneous mutation of the Npc1 gene that causes a defect in lysosome to ER trafficking of cholesterol. These mice also exhibit a similar phenotype to the human disease including cholesterol accumulation in the liver and brain. The model mice show liver injury and neural functional impairment and die before 12 weeks old without proper treatment.

4-week-old NPC mice were treated with HPGCD (4000 mg/kg) once a week until 8.5 weeks of age (5 injections in total), followed by sample collection. Control was treated with saline. The experiments were conducted twice (first; n=6; second: n=4).

Figure 30:
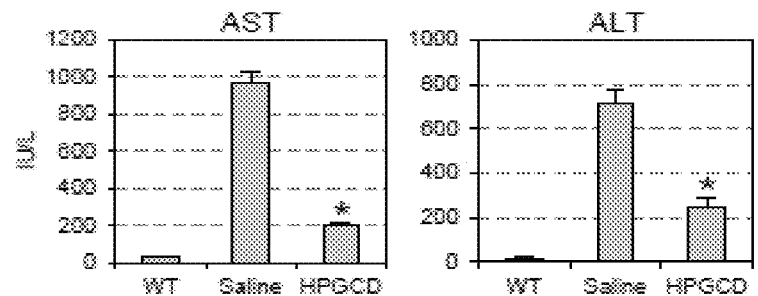
FIG. 30 It shows levels of markers (alanine aminotransferase (ALT) and aspartate aminotransferase (AST)) in the serum.
Figure 31:
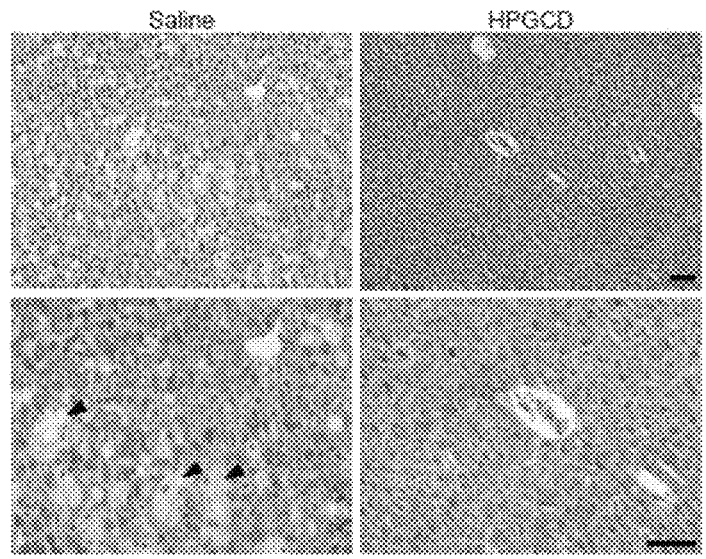
FIG. 31 It represents histological sections of liver from the NPC model mice with HPGCD treatment. Arrow heads indicate lipid-laden parts. Upper images: low magnification (×200), Lower images: high magnification (×400). Scale bars, 50 μm.
Figure 32:
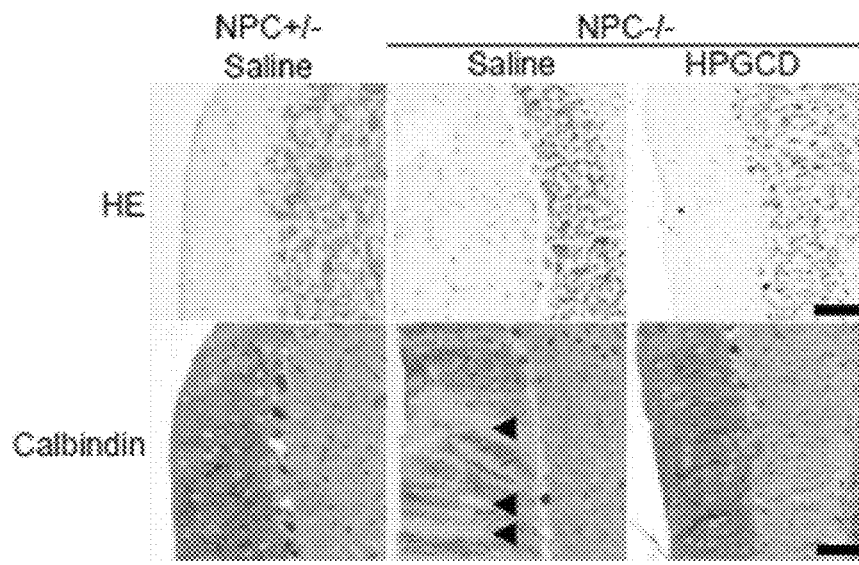
FIG. 32 It represents histological sections of cerebellar vermis from the NPC model mice with HPGCD treatment. The Purkinje cell defect (arrow head) was restored with HPGCD treatment. The sections were stained with H&E (upper panel) or for calbindin immunoreactivity (lower panel).

Following treatment, AST (aspartate aminotransferase) and ALT (alanine aminotransferase), serum markers for liver injury, were markedly and significantly reduced by HPGCD treatment. The results are shown in FIG. 30. Histological analysis revealed a marked morphological improvement in the livers of mice treated with HPGCD (FIG. 31). Deletion of Purkinje cells in the cerebellum was also rescued by the treatment with HPGCD (FIG. 32).

In NPC mice treated with HPGCD abnormal autophagy was restored, and in addition, expression levels of LC3 and insoluble p62 were restored to the normal level in the livers and brains of HPGCD-treated NPC mice (data not shown).

Figure 33:
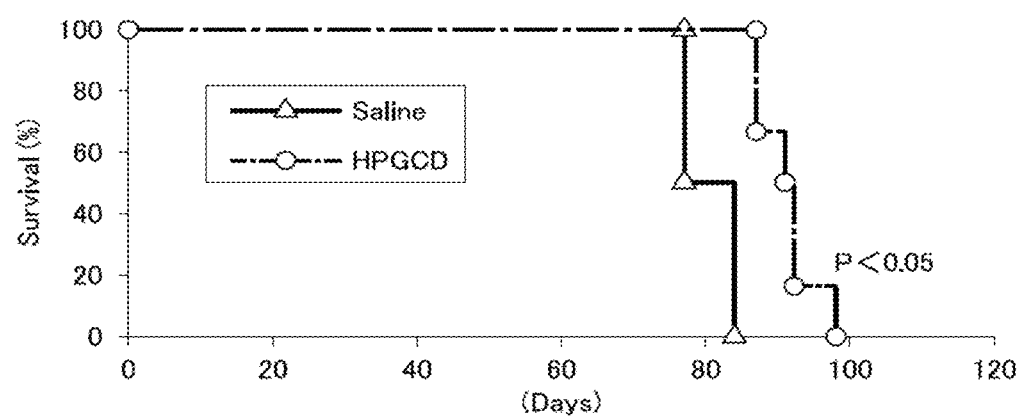
FIG. 33 It shows survival curve for NPC model mice with HPGCD treatment.
Figure 34:
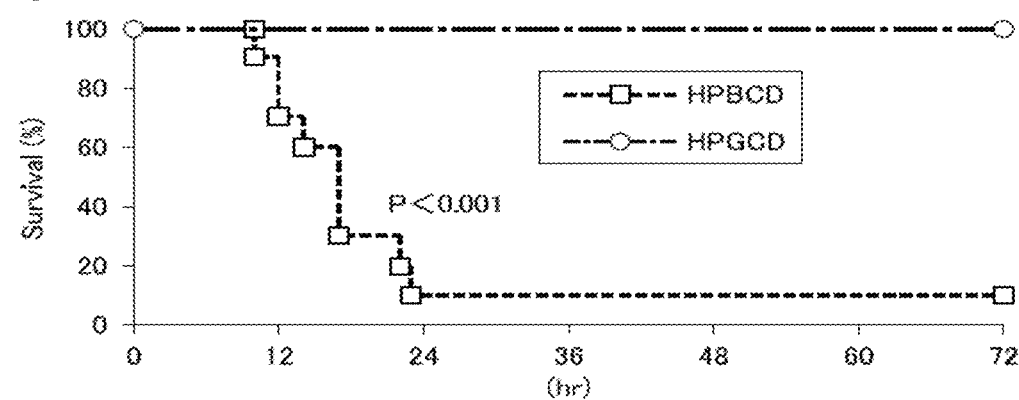
FIG. 34 It shows acute toxicity test of normal mice given HPBCD and HPGCD injections.

To evaluate the effect of HPGCD treatment on NPC mice survival, 4-week-old model mice were injected with HPGCD one a week (HPGCD injection group: n=6, control (saline injection) group: n=6). HPGCD treatment significantly prolonged the NPC mouse survival, as shown in FIG. 33.

Example 10: Toxic Effects of HPBCD and HPGCD

To confirm the excellent safety of HPGCD, acute toxicity was tested using normal mice. 14.4 mM HPBCD or HPGCD were injected in the amount of 19.18 ml/g into subcutaneous tissues of 8-week-old mice (n=10), and then survival rates were calculated. Almost all mice injected with HPBCD dies up to 72 hours after injection, but no mice dies with the HPGCD injection.

The above results indicate that iPS cells without introduced genes are useful cell model for intractable diseases.

To date the inventors have used SeV vectors including the TS12KOS vector to establish more than 1000 iPS cell lines from more than 100 patients with intractable diseases, examples of which are shown in Table 4. In the table, Miyoshi Myopasy used conventional vectors, not TS12KOS vector of the present invention. All iPS cell lines established from the patients exhibited ES cell-like colony morphology and expressed a set of pluripotent markers (data not shown). The SeV-negative status of all iPS cell lines established was confirmed by nested RT-PCR (data not shown), indicating that the lines do not carry the transgenes used for reprogramming.

TABLE 4

| Name of disease | Number of cases |
|---|---|
| Neurologic disease | |
| Alexander's disease | 3 |
| Allan-Herndon-Dudley syndrome | 1 |
| Amyotrophic lateral sclerosis | 8 |
| Bardet-Biedl syndrome | 1 |
| Charcot-Marie-Tooth disease | 1 |
| Familial amyloid polyneuropathy | 6 |
| Huntington's disease | 1 |
| Kii-amyotrophic lateral sclerosis | 2 |
| Kugelberg-Welander disease | 1 |
| Moyamoya disease | 2 |
| Nasu-Hakola disease | 1 |
| Parkinson disease | 1 |
| Pelizaeus-Merzbacher disease | 1 |
| Spinal muscular atrophy | 1 |
| Spinobulbar muscular atrophy | 1 |
| Wolfram syndrome | 1 |
| X-linked α-thalassemia/Mental retardation syndrome | 2 |

TABLE 4-continued

| Name of disease | Number of cases |
|---|---|
| Metabolic disease | |
| Adrenal hyperplasia | 1 |
| Adult-onset type II citrullinemia | 1 |
| Cystinuria | 1 |
| Fabry's disease | 1 |
| Galactosialidosis | 1 |
| Glycogen storage disease type Ia | 2 |
| Glycogen storage disease type II | 1 |
| GM1 gangliosidosis | 1 |
| Hyperlacticacidemia | 1 |
| Krabbe disease | 4 |
| Metachromatic leukodystrophy | 1 |
| Methylmalonic acidemia | 2 |
| Niemann-Pick disease type C | 2 |
| Ornithine transcarbamylase deficiency | 1 |
| Propionic acidemia | 1 |
| Pyruvate dehydrogenase complex deficiency | 1 |
| Tay-Sachs disease | 1 |
| Triglyceride deposit cardiomyovasculopathy | 1 |
| Skin disease | |
| Dermatomyositis | 2 |
| Dyschromatosis universalis hereditaria | 1 |
| Scleroderma | 2 |
| Muscular disease | |
| Central core disease | 1 |
| Congenital fiber type disproportion | 1 |
| Inclusion body myositis | 1 |
| Mitochondrial disease | 2 |
| Miyoshi myopathy* | 1 |
| Muscular dystrophy type becker | 1 |
| Muscular dystrophy type ducehenne | 3 |
| Muscular dystrophy type limb-girdle | 2 |
| Myotonic dystrophy | 1 |
| Kidney disease | |
| Alport's syndrome | 1 |
| Congenital nephrotic syndrome | 1 |

TABLE 4-continued

| Name of disease | Number of cases |
|---|---|
| Galloway-Mowat syndrome | 1 |
| Wolf- Hirschhorn syndrome | 1 |
| Bone and connective tissue disease | |
| Ehlers- Danlos syndrome | 1 |
| Fibrodysplasia ossificans progressiva # | 4 |
| Loeys-Dietz syndrome | 3 |
| Marfan syndrome | 1 |
| Primary osteogenesis imperfecta | 1 |
| Winchester syndrome | 1 |
| Others | |
| Chronic inflammatory neurological cutaneous articular syndrome | 1 |
| Cockayne's syndrome | 1 |
| Daimond-Blackfan Anemia | 3 |
| Prader-Willi syndrome | 1 |
| Pulmonary hypertension | 3 |
| X-linked agammaglobulinemia | 2 |
| Werner syndrome | 1 |
| Wiskott-Aldrich syndrome | 1 |

*, #: Published in Tanaka A. et. al, 2013; Hamasaki M. et. al, 2012, respectively.

The foregoing merely illustrates objects and subjects of the present invention, and does not limit the accompanying Claims. Without departing from the accompanying Claims, various modifications and alterations to the described embodiments will be apparent to those skilled in the art in view of the teachings herein.

INDUSTRIAL APPLICABILITY

The pharmaceutical composition containing hydroxypropyl-γ-cyclodextrin as an active ingredient of the present invention is useful as a therapeutic agent for the lysosomal disease, particularly, Niemann-Pick disease or GM-1 gangliosidosis.

In addition, the iPS cells and the screening method of the present invention can be used for screening therapeutic agents for intractable diseases.

The invention claimed is:

1. A method for treating a lysosomal disease in a subject, comprising administrating to said subject in need thereof a therapeutically effective amount of hydroxypropyl-γ-cyclodextrin as an active ingredient.

2. The method of claim 1, wherein the lysosomal disease is Niemann-Pick disease.

3. The method of claim 1, wherein the lysosomal disease is GM1 gangliosidosis.

4. The method of claim 2, wherein the hydroxypropyl-γ-cyclodextrin is in a pharmaceutically injectable form.

5. The method of claim 3, wherein the hydroxypropyl-γ-cyclodextrin is in a pharmaceutically injectable form.

6. The method of claim 2, wherein the hydroxypropyl-γ-cyclodextrin is injected and administered for a long term.

7. The method of claim 3, wherein the hydroxypropyl-γ-cyclodextrin is injected and administered for a long term.

8. The method of claim 1, wherein the method is provided for delaying the progress of a symptom of the disease.

9. The method of claim 8, wherein the lysosomal disease is Niemann-Pick disease.

10. The method of claim 8, wherein the lysosomal disease is GM1 gangliosidosis.

11. The method of claim 9, wherein the symptom is liver injury or neural functional impairment.

12. The method of claim 10, wherein the symptom is liver injury or neural functional impairment.

* * * * *

SEQUENCE LISTING

<160> NUMBER OF SEQ ID NOS: 56

<210> SEQ ID NO 1
<211> LENGTH: 22
<212> TYPE: DNA
<213> ORGANISM: Artificial Sequence
<220> FEATURE:
<223> OTHER INFORMATION: primer for SeV

<400> SEQUENCE: 1
ggatcactag gtgatatcga gc     22

<210> SEQ ID NO 2
<211> LENGTH: 29
<212> TYPE: DNA
<213> ORGANISM: Artificial Sequence
<220> FEATURE:
<223> OTHER INFORMATION: primer for SeV

<400> SEQUENCE: 2
accagacaag agtttaagag atatgtatc     29

<210> SEQ ID NO 3
<211> LENGTH: 20
<212> TYPE: DNA
<213> ORGANISM: Artificial Sequence

```
<220> FEATURE:
<223> OTHER INFORMATION: primer for SeV

<400> SEQUENCE: 3
tcgagccata tgacagctcg                                              20

<210> SEQ ID NO 4
<211> LENGTH: 36
<212> TYPE: DNA
<213> ORGANISM: Artificial Sequence
<220> FEATURE:
<223> OTHER INFORMATION: primer for SeV

<400> SEQUENCE: 4
gagatatgta ccttttaaa ttttcttgtc ttcttg                             36

<210> SEQ ID NO 5
<211> LENGTH: 24
<212> TYPE: DNA
<213> ORGANISM: Artificial Sequence
<220> FEATURE:
<223> OTHER INFORMATION: primer for Oct3/4

<400> SEQUENCE: 5 gacagggga ggggaggagc tagg                                          24

<210> SEQ ID NO 6
<211> LENGTH: 26
<212> TYPE: DNA
<213> ORGANISM: Artificial Sequence
<220> FEATURE:
<223> OTHER INFORMATION: primer for Oct3/4

<400> SEQUENCE: 6
cttccctcca accagttgcc ccaaac                                       26

<210> SEQ ID NO 7
<211> LENGTH: 26
<212> TYPE: DNA
<213> ORGANISM: Artificial Sequence
<220> FEATURE:
<223> OTHER INFORMATION: primer for SOX2

<400> SEQUENCE: 7
gggaaatggg aggggtgcaa aagagg                                       26

<210> SEQ ID NO 8
<211> LENGTH: 26
<212> TYPE: DNA
<213> ORGANISM: Artificial Sequence
<220> FEATURE:
<223> OTHER INFORMATION: primer for SOX2

<400> SEQUENCE: 8
ttgcgtgagt gtggatggga ttggtg                                       26

<210> SEQ ID NO 9
<211> LENGTH: 30
<212> TYPE: DNA
<213> ORGANISM: Artificial Sequence
<220> FEATURE:
<223> OTHER INFORMATION: primer for KLF4

<400> SEQUENCE: 9
gattacgcgg gctgcggcaa aacctacaca                                   30
```

```
<210> SEQ ID NO 10
<211> LENGTH: 28
<212> TYPE: DNA
<213> ORGANISM: Artificial Sequence
<220> FEATURE:
<223> OTHER INFORMATION: primer for KLF4

<400> SEQUENCE: 10
tgattgtagt gctttctggc tgggctcc                                              28

<210> SEQ ID NO 11
<211> LENGTH: 26
<212> TYPE: DNA
<213> ORGANISM: Artificial Sequence
<220> FEATURE:
<223> OTHER INFORMATION: primer for c-MYC

<400> SEQUENCE: 11
gcgtcctggg aagggagatc cggagc                                                26

<210> SEQ ID NO 12
<211> LENGTH: 26
<212> TYPE: DNA
<213> ORGANISM: Artificial Sequence
<220> FEATURE:
<223> OTHER INFORMATION: primer for c-MYC

<400> SEQUENCE: 12
ttgaggggca tcgtcgcggg aggctg                                                26

<210> SEQ ID NO 13
<211> LENGTH: 25
<212> TYPE: DNA
<213> ORGANISM: Artificial Sequence
<220> FEATURE:
<223> OTHER INFORMATION: primer for NANOG

<400> SEQUENCE: 13
cagccccgat tcttccacca gtccc                                                 25

<210> SEQ ID NO 14
<211> LENGTH: 25
<212> TYPE: DNA
<213> ORGANISM: Artificial Sequence
<220> FEATURE:
<223> OTHER INFORMATION: primer for NANOG

<400> SEQUENCE: 14
cggaagattc ccagtcgggt tcacc                                                 25

<210> SEQ ID NO 15
<211> LENGTH: 24
<212> TYPE: DNA
<213> ORGANISM: Artificial Sequence
<220> FEATURE:
<223> OTHER INFORMATION: primer for GDF3

<400> SEQUENCE: 15
cttatgctac gtaaaggagc tggg                                                  24

<210> SEQ ID NO 16
<211> LENGTH: 24
<212> TYPE: DNA
<213> ORGANISM: Artificial Sequence
<220> FEATURE:
<223> OTHER INFORMATION: primer for DF3
```

-continued

```
<400> SEQUENCE: 16
gtgccaaccc aggtcccgga agtt                                            24

<210> SEQ ID NO 17
<211> LENGTH: 24
<212> TYPE: DNA
<213> ORGANISM: Artificial Sequence
<220> FEATURE:
<223> OTHER INFORMATION: primer for REX1

<400> SEQUENCE: 17
cagatcctaa acagctcgca gaat                                            24

<210> SEQ ID NO 18
<211> LENGTH: 23
<212> TYPE: DNA
<213> ORGANISM: Artificial Sequence
<220> FEATURE:
<223> OTHER INFORMATION: primer for REX1

<400> SEQUENCE: 18
gcgtacgcaa attaaagtcc aga                                             23

<210> SEQ ID NO 19
<211> LENGTH: 20
<212> TYPE: DNA
<213> ORGANISM: Artificial Sequence
<220> FEATURE:
<223> OTHER INFORMATION: primer for SALL4

<400> SEQUENCE: 19 aaacccagc acatcaactc                                                  20

<210> SEQ ID NO 20
<211> LENGTH: 19
<212> TYPE: DNA
<213> ORGANISM: Artificial Sequence
<220> FEATURE:
<223> OTHER INFORMATION: primer for SALL4

<400> SEQUENCE: 20
gtcattccct gggtggttc                                                  19

<210> SEQ ID NO 21
<211> LENGTH: 25
<212> TYPE: DNA
<213> ORGANISM: Artificial Sequence
<220> FEATURE:
<223> OTHER INFORMATION: primer for DNMT3b

<400> SEQUENCE: 21
tgctgctcac agggcccgat acttc                                           25

<210> SEQ ID NO 22
<211> LENGTH: 28
<212> TYPE: DNA
<213> ORGANISM: Artificial Sequence
<220> FEATURE:
<223> OTHER INFORMATION: primer for DNMT3b

<400> SEQUENCE: 22
tcctttcgag ctcagtgcac cacaaaac                                        28

<210> SEQ ID NO 23
```

<211> LENGTH: 26
<212> TYPE: DNA
<213> ORGANISM: Artificial Sequence
<220> FEATURE:
<223> OTHER INFORMATION: primer for SOX17

<400> SEQUENCE: 23
cgctttcatg gtgtgggcta aggacg                                          26

<210> SEQ ID NO 24
<211> LENGTH: 26
<212> TYPE: DNA
<213> ORGANISM: Artificial Sequence
<220> FEATURE:
<223> OTHER INFORMATION: primer for SOX17

<400> SEQUENCE: 24
tagttggggt ggtcctgcat gtgctg                                          26

<210> SEQ ID NO 25
<211> LENGTH: 19
<212> TYPE: DNA
<213> ORGANISM: Artificial Sequence
<220> FEATURE:
<223> OTHER INFORMATION: primer for CXCR4

<400> SEQUENCE: 25
caccgcatct ggagaacca                                                  19

<210> SEQ ID NO 26
<211> LENGTH: 19
<212> TYPE: DNA
<213> ORGANISM: Artificial Sequence
<220> FEATURE:
<223> OTHER INFORMATION: primer for CXCR4

<400> SEQUENCE: 26
ctgacaggtg cagcctgta                                                  19

<210> SEQ ID NO 27
<211> LENGTH: 27
<212> TYPE: DNA
<213> ORGANISM: Artificial Sequence
<220> FEATURE:
<223> OTHER INFORMATION: primer for HNF4a

<400> SEQUENCE: 27
ctgctcggag ccaccaagag atccatg                                         27

<210> SEQ ID NO 28
<211> LENGTH: 25
<212> TYPE: DNA
<213> ORGANISM: Artificial Sequence
<220> FEATURE:
<223> OTHER INFORMATION: primer for HNF4a

<400> SEQUENCE: 28
atcatctgcc acgtgatgct ctgca                                           25

<210> SEQ ID NO 29
<211> LENGTH: 18
<212> TYPE: DNA
<213> ORGANISM: Artificial Sequence
<220> FEATURE:
<223> OTHER INFORMATION: primer for HNF6

<400> SEQUENCE: 29

```
cgctccgctt agcagcat                                                    18

<210> SEQ ID NO 30
<211> LENGTH: 20
<212> TYPE: DNA
<213> ORGANISM: Artificial Sequence
<220> FEATURE:
<223> OTHER INFORMATION: primer for HNF6

<400> SEQUENCE: 30
ccctgctgaa gtgtgtgtct                                                  20

<210> SEQ ID NO 31
<211> LENGTH: 20
<212> TYPE: DNA
<213> ORGANISM: Artificial Sequence
<220> FEATURE:
<223> OTHER INFORMATION: primer for AFP

<400> SEQUENCE: 31
agaacctgtc acaagctgtg                                                  20

<210> SEQ ID NO 32
<211> LENGTH: 20
<212> TYPE: DNA
<213> ORGANISM: Artificial Sequence
<220> FEATURE:
<223> OTHER INFORMATION: primer for AFP

<400> SEQUENCE: 32
gacagcaagc tgaggatgtc                                                  20

<210> SEQ ID NO 33
<211> LENGTH: 26
<212> TYPE: DNA
<213> ORGANISM: Artificial Sequence
<220> FEATURE:
<223> OTHER INFORMATION: primer for ALB

<400> SEQUENCE: 33
cctttggcac aatgaagtgg gtaacc                                           26

<210> SEQ ID NO 34
<211> LENGTH: 25
<212> TYPE: DNA
<213> ORGANISM: Artificial Sequence
<220> FEATURE:
<223> OTHER INFORMATION: primer for ALB

<400> SEQUENCE: 34
cagcagtcag ccatttcacc atagg                                            25

<210> SEQ ID NO 35
<211> LENGTH: 18
<212> TYPE: DNA
<213> ORGANISM: Artificial Sequence
<220> FEATURE:
<223> OTHER INFORMATION: primer for b-Action

<400> SEQUENCE: 35
caaccgcgag aagatgac                                                    18

<210> SEQ ID NO 36
<211> LENGTH: 18
<212> TYPE: DNA
```

```
<213> ORGANISM: Artificial Sequence
<220> FEATURE:
<223> OTHER INFORMATION: primer for b-Actiin

<400> SEQUENCE: 36
aggaaggctg gaagagtg                                                 18

<210> SEQ ID NO 37
<211> LENGTH: 20
<212> TYPE: DNA
<213> ORGANISM: Artificial Sequence
<220> FEATURE:
<223> OTHER INFORMATION: primer for PAX6

<400> SEQUENCE: 37
gtccatcttt gcttgggaaa                                               20

<210> SEQ ID NO 38
<211> LENGTH: 20
<212> TYPE: DNA
<213> ORGANISM: Artificial Sequence
<220> FEATURE:
<223> OTHER INFORMATION: primer for PAX6

<400> SEQUENCE: 38
tagccaggtt gcgaagaact                                               20

<210> SEQ ID NO 39
<211> LENGTH: 20
<212> TYPE: DNA
<213> ORGANISM: Artificial Sequence
<220> FEATURE:
<223> OTHER INFORMATION: primer for ZIC1

<400> SEQUENCE: 39
ctggctgtgg caaggtcttc                                               20

<210> SEQ ID NO 40
<211> LENGTH: 19
<212> TYPE: DNA
<213> ORGANISM: Artificial Sequence
<220> FEATURE:
<223> OTHER INFORMATION: primer for ZIC1

<400> SEQUENCE: 40
cagccctcaa actcgcact                                                19

<210> SEQ ID NO 41
<211> LENGTH: 20
<212> TYPE: DNA
<213> ORGANISM: Artificial Sequence
<220> FEATURE:
<223> OTHER INFORMATION: primer for ZNF 521

<400> SEQUENCE: 41
acctccgtgt ccagtacgac                                               20

<210> SEQ ID NO 42
<211> LENGTH: 20
<212> TYPE: DNA
<213> ORGANISM: Artificial Sequence
<220> FEATURE:
<223> OTHER INFORMATION: primer for ZNF 521

<400> SEQUENCE: 42
atgtcagggg tttgttgagc                                               20
```

<210> SEQ ID NO 43
<211> LENGTH: 24
<212> TYPE: DNA
<213> ORGANISM: Artificial Sequence
<220> FEATURE:
<223> OTHER INFORMATION: primer for OTX2

<400> SEQUENCE: 43
gccaatcctt ggttgaatct tagg                                              24

<210> SEQ ID NO 44
<211> LENGTH: 25
<212> TYPE: DNA
<213> ORGANISM: Artificial Sequence
<220> FEATURE:
<223> OTHER INFORMATION: primer for OTX2

<400> SEQUENCE: 44
caatcagtca cacaattcac acagc                                             25

<210> SEQ ID NO 45
<211> LENGTH: 22
<212> TYPE: DNA
<213> ORGANISM: Artificial Sequence
<220> FEATURE:
<223> OTHER INFORMATION: primer for NEUROGENIN1

<400> SEQUENCE: 45
agcctgccca aagacttgct cc                                                22

<210> SEQ ID NO 46
<211> LENGTH: 24
<212> TYPE: DNA
<213> ORGANISM: Artificial Sequence
<220> FEATURE:
<223> OTHER INFORMATION: primer for NEUROGENIN1

<400> SEQUENCE: 46
cctaacaagc ggctcaggta tccc                                              24

<210> SEQ ID NO 47
<211> LENGTH: 20
<212> TYPE: DNA
<213> ORGANISM: Artificial Sequence
<220> FEATURE:
<223> OTHER INFORMATION: primer for HES5

<400> SEQUENCE: 47
ctcagcccca aagagaaaaa                                                   20

<210> SEQ ID NO 48
<211> LENGTH: 20
<212> TYPE: DNA
<213> ORGANISM: Artificial Sequence
<220> FEATURE:
<223> OTHER INFORMATION: primer for HES5

<400> SEQUENCE: 48
gacagccatc tccaggatgt                                                   20

<210> SEQ ID NO 49
<211> LENGTH: 20
<212> TYPE: DNA
<213> ORGANISM: Artificial Sequence
<220> FEATURE:

<223> OTHER INFORMATION: primer for exon5 of NPC1

<400> SEQUENCE: 49
tgcctcgtga attacagcaa                                      20

<210> SEQ ID NO 50
<211> LENGTH: 19
<212> TYPE: DNA
<213> ORGANISM: Artificial Sequence
<220> FEATURE:
<223> OTHER INFORMATION: primer for exon 5 of NPC1

<400> SEQUENCE: 50
caagcactgg tgagccact                                       19

<210> SEQ ID NO 51
<211> LENGTH: 20
<212> TYPE: DNA
<213> ORGANISM: Artificial Sequence
<220> FEATURE:
<223> OTHER INFORMATION: primer for exon 13 of NPC1

<400> SEQUENCE: 51
gcccgagcag acctagaaat                                      20

<210> SEQ ID NO 52
<211> LENGTH: 20
<212> TYPE: DNA
<213> ORGANISM: Artificial Sequence
<220> FEATURE:
<223> OTHER INFORMATION: primer for exon 13 of NPC1

<400> SEQUENCE: 52
atgctgagcc ctgtgagaat                                      20

<210> SEQ ID NO 53
<211> LENGTH: 20
<212> TYPE: DNA
<213> ORGANISM: Artificial Sequence
<220> FEATURE:
<223> OTHER INFORMATION: primer for exon 22 of NPC1

<400> SEQUENCE: 53
ggtgagtctt gtagacagcc                                      20

<210> SEQ ID NO 54
<211> LENGTH: 20
<212> TYPE: DNA
<213> ORGANISM: Artificial Sequence
<220> FEATURE:
<223> OTHER INFORMATION: primer for exon 22 of NPC1

<400> SEQUENCE: 54
atggcgatgg tggcacacat                                      20

<210> SEQ ID NO 55
<211> LENGTH: 20
<212> TYPE: DNA
<213> ORGANISM: Artificial Sequence
<220> FEATURE:
<223> OTHER INFORMATION: primer for exon 23 of NPC1

<400> SEQUENCE: 55
caggcttttg gctgtgtgta                                      20

```
<210> SEQ ID NO 56
<211> LENGTH: 21
<212> TYPE: DNA
<213> ORGANISM: Artificial Sequence
<220> FEATURE:
<223> OTHER INFORMATION: primer for exon 23 of NPC1

<400> SEQUENCE: 56
ggattacttt gtggtgcgac t                                              21
```